(12) United States Patent
Van Geel-Schutten et al.

(10) Patent No.: US 6,486,314 B1
(45) Date of Patent: Nov. 26, 2002

(54) GLUCAN INCORPORATING 4-, 6-, AND 4, 6- LINKED ANHYDROGLUCOSE UNITS

(75) Inventors: Gerritdina Hendrika Van Geel-Schutten, Driebergen-Rijsenburg (NL); Lubbert Dijkhuizen, Zuidlaren (NL); Hakim Rahaoui, Amersfoort (NL); Robert-Jan Leer, Veenendaal (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 57 days.

(21) Appl. No.: 09/604,957

(22) Filed: Jun. 28, 2000

(30) Foreign Application Priority Data

May 25, 2000 (EP) ............................................. 00201871

(51) Int. Cl.$^7$ ................................................ C07H 1/100
(52) U.S. Cl. ................................. 536/123.12; 536/55.1
(58) Field of Search ........................ 536/123.1, 123.12, 536/55.1, 55, 18.7; 514/54

(56) References Cited

PUBLICATIONS

G.H. van Geel–Schutten et al., "Exopolysaccharide Production by *Lactobacillus reuteri*, Involving Sucrase Type of Enzymes, "*Med. Fac. Landbouww*, Univ. Gent, V. 65, No. 3a, 2000, pp. 197–201.

G.H. Van Geel–Schutten et al., "Biochemical and Structural Characterization of the Glucan and Fructan Exopolysaccharides Synthesized by the *Lactobacillus reuteri* Wild–Type Strain and by Mutant Strains," *Applied and Environmental Microbiology*, V. 65, No. 7, Jul. 1999, pp. 3008–3014.

Vincent Monchois et al., "Cloning and Sequencing of a Gene Coding for a Novel Dextransucrase from *Leuconostoc Mesenteroides* NRRL B–1299 Synthesizing Only α(1–6) and α(1–3) Linkages," *Gene* (Amsterdam), V. 182, No. 1–2, 1996, pp. 23–32.

Christine L. Simpson et al., "*Streptococcus salivarius* ATCC 25975 Possesses at Least Two Genes Coding for Primer- –Independent Glucosyltransferases," *Infection and Immunity*, V. 63, No. 2, 1995, pp. 609–621.

*Primary Examiner*—James O. Wilson
*Assistant Examiner*—Patrick Lewis
(74) *Attorney, Agent, or Firm*—Young & Thompson

(57) ABSTRACT

The present invention describes a protein having glucosyltransferase activity. This protein is derived from lactobacilli, which are food-grade microorganisms with the Generally Recognized As Safe (GRAS) status. The protein produces a glucan with a unique structure having 4-linked, 6-lined and 4,6-linked anhydroglucose units or in the presence of suitable acceptors, oligosaccharides. According to the invention lactobacilli capable of producing this glucan using the novel glucosyltransferase can be used as a probiotic or symbiotic.

2 Claims, 15 Drawing Sheets

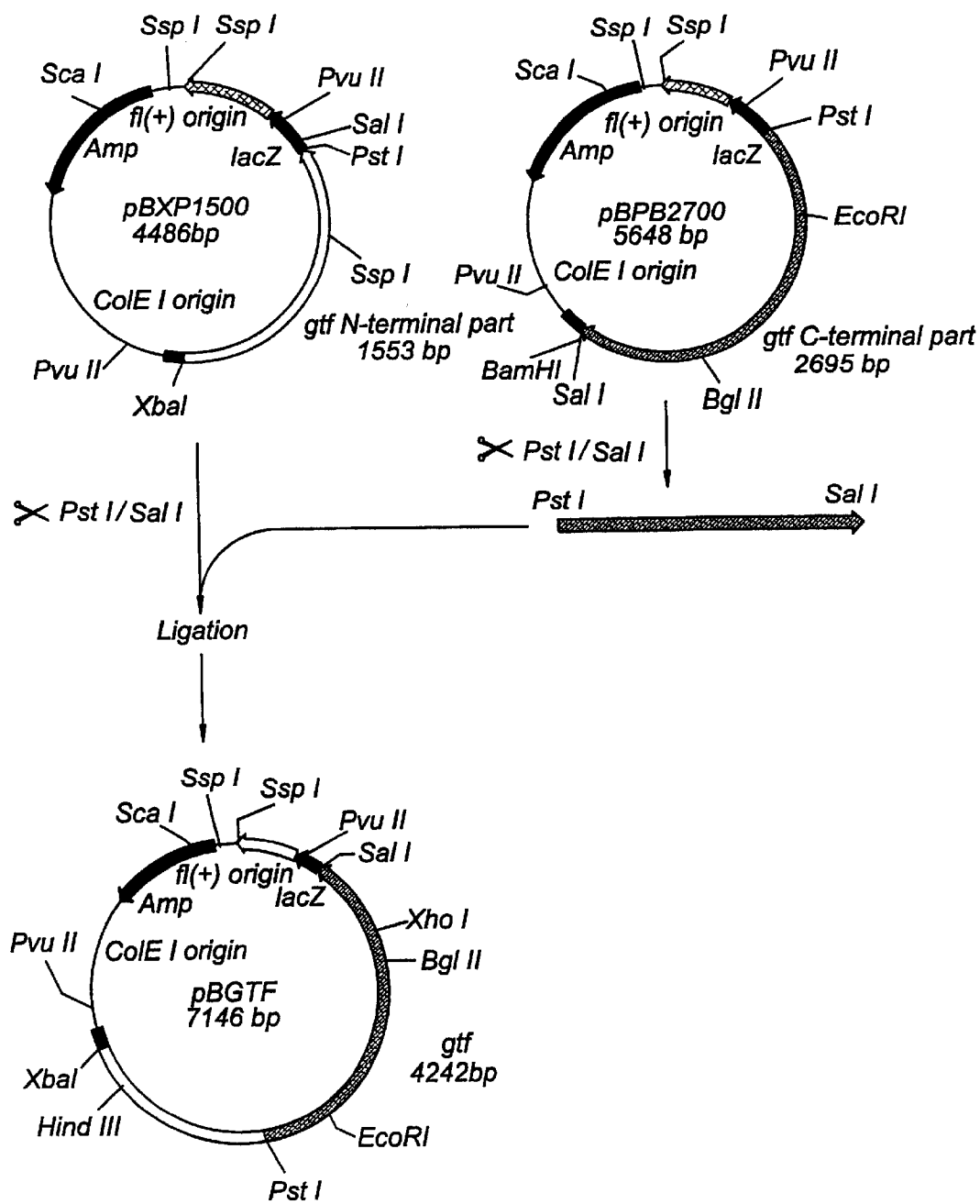

Fig. 3A (SEQ ID NO:1)

```
1         TCTACTTCTACACCTGTTTCTGTTTTGCCATCTAATAATACTGAAAAACAAGCTAAAAAT
1   ORF2P  S  T  S  T  P  V  S  V  L  P  S  N  N  T  E  K  Q  A  K  N
       (SEQ ID NO:2)

61        TATAATGAGCAAGACAAAGGAAACTATGGGAATATTGATACTGCTTACTTTAGCAATAAT
21         Y  N  E  Q  D  K  G  N  Y  G  N  I  D  T  A  Y  F  S  N  N

121       CAATTGCATGTTTCAGGATGGAATGCAACGAACGCATCTCAAGGAACAAACAGTCGACAA
41         Q  L  H  V  S  G  W  N  A  T  N  A  S  Q  G  T  N  S  R  Q

181       ATCATTGTGCGTGATATCACAACCAATAATGAATTAGGTCGCACTGATGTAACAAACAAT
61         I  I  V  R  D  I  T  T  N  N  E  L  G  R  T  D  V  T  N  N

241       GTTGCACGCCCAGACGTTAAGAATGTTCATAATGTTTATAACGCTGATAATTCTGGATTT
81         V  A  R  P  D  V  K  N  V  H  N  V  Y  N  A  D  N  S  G  F

301       GATGTTAATGTCAATATTGACTTTAGCAAGATGAAAGATTATCGGGATTCAATTGAAATT
101        D  V  N  V  N  I  D  F  S  K  M  K  D  Y  R  D  S  I  E  I

361       GTTAGTCGATACAGTGGAAACGGTAAATCTGTTGACTGGTGGTCCCAACCGATCACTTTT
121        V  S  R  Y  S  G  N  G  K  S  V  D  W  W  S  Q  P  I  T  F

421       GACAAAAACAACTATGCTTATCTTGATACATTTGAAGTGAAAAATGGCGAATTACATGCA
141        D  K  N  N  Y  A  Y  L  D  T  F  E  V  K  N  G  E  L  H  A

481       ACCGGATGGAATGCTACTAATAGTGCGATTAACTATAATCACCATTTTGTGATTTTGTTT
161        T  G  W  N  A  T  N  S  A  I  N  Y  N  H  H  F  V  I  L  F

541       GATCAAACGAATGGTAAAGAAGTAGCACGACAAGAAGTTCGTGAAGGTCAATCACGCCCA
181        D  Q  T  N  G  K  E  V  A  R  Q  E  V  R  E  G  Q  S  R  P

601       GATGTTGCTAAGGTATATCCACAAGTAGTTGGTGCTGCCAACTCAGGCTTTAATGTGACA
201        D  V  A  K  V  Y  P  Q  V  V  G  A  A  N  S  G  F  N  V  T

661       TTTAATATCAGTGATTTAGATTATACTCACCAGTACCAAGTTCTTAGTCGTTACAGCAAT
221        F  N  I  S  D  L  D  Y  T  H  Q  Y  Q  V  L  S  R  Y  S  N

721       TCTGATAATGGCGAAGGTGATAACGTTACCTACTGGTTTAATCCACAATCCATTGCTCCT
241        S  D  N  G  E  G  D  N  V  T  Y  W  F  N  P  Q  S  I  A  P

781       GCTAATCAAAGTAACCAGGGTTATCTAGACTCATTTGATATTAGTAAAAATGGTGAAGTA
261        A  N  Q  S  N  Q  G  Y  L  D  S  F  D  I  S  K  N  G  E  V

841       ACAGTAACTGGATGGAACGCTACTGACTTGTCAGAATTACAAAACAACCATTATGTGATT
281        T  V  T  G  W  N  A  T  D  L  S  E  L  Q  N  N  H  Y  V  I
```

Fig.3B

```
 901  CTATTTGATCAGACAGCAGGCAAACAAGTTGCATCTGCTAAAGCTGATTTAATTTCACGT
 301   L  F  D  Q  T  A  G  K  Q  V  A  S  A  K  A  D  L  I  S  R

961  CCAGATGTTGCTAAAGCTTATCCACAGTAAAAACAGCTACAAATTCTGGCTTCAAGGTAA
 321   P  D  V  A  K  A  Y  P  Q  *

1021  CATTTAAGGTTAATAACTTACAACCGGGTCACCAATACAGCGTTGTAAGTCGTTTCTCTG

1081  CCGATGAAAATGGTAATGGTAATGATAAGCGCCATACAGATTACTGGTTTAGTCCAGTAA

1141  TATTAAACCAGACTGCTTCAAACATTGATACTATTACAATGACATCTAATGGTTTACATA rbs
1201  TTGCAGGTTGGATGGCAAGTGATAACTCAATTAATGAAACAACTCCATACGCTATTATCC
           GTFA⇒   M  A  S  D  N  S  I  N  E  T  T  P  Y  A  I  I
           (SEQ ID NO:3)
                rbs
1261  TCAATAATGGAAAGAAGTTACTCGTCAAAAGATGAGCTTAACCGCCCGTCCAGATGTAG
       L  N  N  G  K  E  V  T  R  Q  K  M  S  L  T  A  R  P  D  V 1321  CAGCAGTATATCCTTCACTTTATAATAGTGCTGTTAGTGGTTTTGACACTACTATTAAAT
 10    A  A  V  Y  P  S  L  Y  N  S  A  V  S  G  F  D  T  T  I  K 1381  TGACTAATGATCAATATCAAGCGCTTAATGGCCAATTACAAGTATTGTTACGTTTTTCTA
 30    L  T  N  D  Q  Y  Q  A  L  N  G  Q  L  Q  V  L  L  R  F  S 1441  AAGCTGCTGATGGTAATCCAAGTGGTGATAATACTGTAACTGATCAATTTAGTAAAAATT
 50    K  A  A  D  G  N  P  S  G  D  N  T  V  T  D  Q  F  S  K  N 1501  ATGCAACTACTGGTGGAAACTTTGACTATGTAAAAGTAAATGGTAATCAAGTTGAATTTA
 70    Y  A  T  T  G  G  N  F  D  Y  V  K  V  N  G  N  Q  V  E  F 1561  GTGGTTGGCACGCAACTAACCAATCAAATGATAAAGATTCACAATGGATTATTGTTTTAG
 90    S  G  W  H  A  T  N  Q  S  N  D  K  D  S  Q  W  I  I  V  L 1621  TTAATGGTAAGGAAGTAAAGCGTCAATTAGTTAATGATACTAAAGAGGGAGCTGCTGGCT
110    V  N  G  K  E  V  K  R  Q  L  V  N  D  T  K  E  G  A  A  G 1681  TCAACCGAAACGATGTCTACAAAGTAAATCCAGCTATTGAAAACAGTTCTATGTCTGGAT
130    F  N  R  N  D  V  Y  K  V  N  P  A  I  E  N  S  S  M  S  G 1741  TCCAAGGCATTATTACTTTACCTGTGACAGTTAAAAACGAAAATGTCCAACTTGTTCATC
150    F  Q  G  I  I  T  L  P  V  T  V  K  N  E  N  V  Q  L  V  E
```

Fig.3C

```
1801  GGTTTAGTAACGATGTGAAGACTGGTGAAGGTAACTATGTTGATTTCTGGTCAGAGCTAA
170    R  F  S  N  D  V  K  T  G  E  G  N  Y  V  D  F  W  S  E  L

1861  TGCCTGTTAAGGATAGCTTCCAAAAGGGGAATGGCCCACTTAAGCAATTTGGCTTACAAA
190    M  P  V  K  D  S  F  Q  K  G  N  G  P  L  K  Q  F  G  L  Q

1921  CTATTAACGGTCAACAATATTATATTGACCCAACAACTGGTCAACCACGTAAGAATTTCT
210    T  I  N  G  Q  Q  Y  Y  I  D  P  T  T  G  Q  P  R  K  N  F

1981  TATTACAAAGTGGAAATAATTGGATTTACTTTGATAGTGATACTGGTGTGGGTACTAATG
230    L  L  Q  S  G  N  N  W  I  Y  F  D  S  D  T  G  V  G  T  N

2041  CACTTGAATTACAATTTGCAAAGGGAACTGTTTCATCTAATGAACAATACCGTAACGGTA
250    A  L  E  L  Q  F  A  K  G  T  V  S  S  N  E  Q  Y  R  N  G

2101  ATGCAGCTTACAGTTATGATGACAAGAGTATCGAAAATGTAAATGGTTACTTAACAGCAG
270    N  A  A  Y  S  Y  D  D  K  S  I  E  N  V  N  G  Y  L  T  A

2161  ATACATGGTACCGTCCAAAACAGATCTTAAAGGATGGAACTACCTGGACTGACTCAAAAG
290    D  T  W  Y  R  P  K  Q  I  L  K  D  G  T  T  W  T  D  S  K

2221  AAACAGATATGCGACCAATCTTGATGGTATGGTGGCCTAATACTCTTACCCAAGCATACT
310    E  T  D  M  R  P  I  L  M  V  W  W  P  N  T  L  T  Q  A  Y

2281  ACCTTAATTACATGAAACAACATGGTAATTTATTACCATCTGCTTTACCATTCTTTAATG
330    Y  L  N  Y  M  K  Q  H  G  N  L  L  P  S  A  L  P  F  F  N

2341  CGGATGCTGATCCTGCAGAATTAAATCATTATTCCGAAATTGTGCAACAAAATATTGAAA
350    A  D  A  D  P  A  E  L  N  H  Y  S  E  I  V  Q  Q  N  I  E

2401  AACGAATTAGTGAAACCGGAAATACTGATTGGTTACGTACTTTAATGCACGATTTTGTTA
370    K  R  I  S  E  T  G  N  T  D  W  L  R  T  L  M  H  D  F  V

2461  CTAACAATCCGATGTGGAATAAGGATAGTGAAAATGTTAACTTTAGTGGTATTCAATTCC
390    T  N  N  P  M  W  N  K  D  S  E  N  V  N  F  S  G  I  Q  F

2521  AAGGCGGATTCTTAAAGTATGAAAACTCAGATTTAACGCCTTATGCTAACTCTGATTATC
410    Q  G  G  F  L  K  Y  E  N  S  D  L  T  P  Y  A  N  S  D  Y

2581  GCTTACTTGGTCGGATGCCAATCAATATTAAGGATCAAACATATCGGGGACAAGAATTCC
430    R  L  L  G  R  M  P  I  N  I  K  D  Q  T  Y  R  G  Q  E  F
```

Fig.3D

```
2641  TACTTGCTAACGATATTGATAACTCTAATCCTGTTGTTCAAGCAGAACAATTAAACTGGT
450    L  L  A  N  D  I  D  N  S  N  P  V  V  Q  A  E  Q  L  N  W

2701  TATACTATCTCTTGAACTTTGGAACGATCACAGCTAATAATGATCAAGCTAATTTTGATT
470    L  Y  Y  L  L  N  F  G  T  I  T  A  N  N  D  Q  A  N  F  D

2761  CTGTACGGGTAGATGCACCGGATAATATTGATGCCGATCTTATGAATATCGCTCAGGACT
490    S  V  R  V  D  A  P  D  N  I  D  A  D  L  M  N  I  A  Q  D

2821  ACTTTAATGCTGCATATGGTATGGACTCAGATGCTGTCTCAAATAAGCATATTAATATTC
510    Y  F  N  A  A  Y  G  M  D  S  D  A  V  S  N  K  H  I  N  I

2881  TTGAAGACTGGAATCATGCTGATCCGGAATACTTTAATAAGATCGGAAATCCACAATTGA
530    L  E  D  W  N  H  A  D  P  E  Y  F  N  K  I  G  N  P  Q  L

2941  CAATGGATGATACTATTAAGAATTCCCTGAATCATGGCTTTCAGATGCAACTAATCGTT
550    T  M  D  D  T  I  K  N  S  L  N  H  G  L  S  D  A  T  N  R

3001  GGGGATTAGATGCAATTGTTCATCAGTCATTAGCTGATCGTGAAAATAATTCCACGGAAA
570    W  G  L  D  A  I  V  H  Q  S  L  A  D  R  E  N  N  S  T  E

3061  ATGTTGTAATTCCTAATTACAGTTTCGTTCGGGCTCACGATAATAATTCTCAAGATCAAA
590    N  V  V  I  P  N  Y  S  F  V  R  A  H  D  N  N  S  Q  D  Q

3121  TTCAAAATGCTATTCGTGATGTAACAGGCAAAGATTACCATACTTTCACTTTTGAAGATG
610    I  Q  N  A  I  R  D  V  T  G  K  D  Y  H  T  F  T  F  E  D

3181  AGCAAAAGGGTATTGATGCGTACATTCAAGATCAAAATTCAACAGTGAAGAAATATAACC
630    E  Q  K  G  I  D  A  Y  I  Q  D  Q  N  S  T  V  K  K  Y  N

3241  TTTATAATATTCCGGCTTCATACGCAATTCTTTTAACTAACAAGGATACAATTCCACGTG
650    L  Y  N  I  P  A  S  Y  A  I  L  L  T  N  K  D  T  I  P  R

3301  TATACTATGGTGACTTGTATACTGATGGTGGCCAATACATGGAACATCAAACACGTTACT
670    V  Y  Y  G  D  L  Y  T  D  G  G  Q  Y  M  E  H  Q  T  R  Y

3361  ATGATACTTTAACGAACCTGCTTAAATCACGAGTTAAGTATGTTGCCGGTGGCCAATCAA
690    Y  D  T  L  T  N  L  L  K  S  R  V  K  Y  V  A  G  G  Q  S

3421  TGCAAACAATGAGCGTTGGCGGCAATAATAATCTTACTAGTGTTCGTTATGGTAAG
710    M  Q  T  M  S  V  G  G  N  N  N  I  L  T  S  V  R  Y  G  K
```

Fig.3E

```
3481   GTGCGATGACAGCTACTGATACTGGTACTGATGAAACCAGAACACAAGGTATTGGGGTTG
730     G  A  M  T  A  T  D  T  G  T  D  E  T  R  T  Q  G  I  G  V

3541   TTGTAAGTAATACGCCAAATCTAAAGCTAGGTGTCAACGATAAAGTAGTTCTTCATATGG
750     V  V  S  N  T  P  N  L  K  L  G  V  N  D  K  V  V  L  H  M

3601   GAGCTGCGCACAAGAACCAACAATATCGGGCAGCCGTGTTGACGACAACTGATGGAGTCA
770     G  A  A  H  K  N  Q  Q  Y  R  A  A  V  L  T  T  T  D  G  V

3661   TTAATTATACTTCTGATCAAGGGGCACCGGTTGCAATGACTGACGAGAACGGTGATCTAT
790     I  N  Y  T  S  D  Q  G  A  P  V  A  M  T  D  E  N  G  D  L

3721   ACTTATCTAGTCATAACCTAGTTGTTAATGGTAAAGAAGAAGCAGATACAGCTGTTCAAG
810     Y  L  S  S  H  N  L  V  V  N  G  K  E  E  A  D  T  A  V  Q

3781   GTTATGCTAACCCTGATGTTTCAGGATATCTTGCTGTATGGGTACCAGTTGGAGCAAGTG
830     G  Y  A  N  P  D  V  S  G  Y  L  A  V  W  V  P  V  G  A  S

3841   ATAACCAAGATGCTCGAACTGCTCCATCTACTGAAAAGAATAGTGGTAACTCTGCATACA
850     D  N  Q  D  A  R  T  A  P  S  T  E  K  N  S  G  N  S  A  Y

3901   GAACAAATGCTGCTTTTGATTCAAATGTTATTTTTGAAGCCTTTTCTAACTTTGTCTATA
870     R  T  N  A  A  F  D  S  N  V  I  F  E  A  F  S  N  F  V  Y

3961   CACCAACAAAGGAAAGTGAACGTGCTAATGTTCGAATTGCCCAAAATGCTGATTTCTTTG
890     T  P  T  K  E  S  E  R  A  N  V  R  I  A  Q  N  A  D  F  F

4021   CTTCATTAGGTTTTACTTCTTTCGAGATGGCGCCACAATATAATTCAAGTAAAGATCGCA
910     A  S  L  G  F  T  S  F  E  M  A  P  Q  Y  N  S  S  K  D  R

4081   CATTCCTAGATTCAACAATTGATAACGGATATGCGTTTACTGATCGTTATGATCTTGGAA
930     T  F  L  D  S  T  I  D  N  G  Y  A  F  T  D  R  Y  D  L  G

4141   TGAGTGAGCCTAATAAGTACGGAACAGATGAAGATCTACGTAATGCCATTCAAGCGCTCC
950     M  S  E  P  N  K  Y  G  T  D  E  D  L  R  N  A  I  Q  A  L

4201   ATAAAGCTGGCTTACAAGTAATGGCGGATTGGGTTCCTGACCAAATCTATAACCTTCCTG
970     H  K  A  G  L  Q  V  M  A  D  W  V  P  D  Q  I  Y  N  L  P

4261   GAAAAGAAGTTGCTACAGTCACTCGAGTAGATGATCGTGGTAATGTATGGAAAGATGCTA
990     G  K  E  V  A  T  V  T  R  V  D  D  R  G  N  V  W  K  D  A
```

Fig. 3F

```
4321   TCATTAATAATAATCTGTATGTTGTTAATACTATTGGTGGTGGCAATACCAGAAGAAGT
1010    I  I  N  N  N  L  Y  V  V  N  T  I  G  G  G  E  Y  Q  K  K

4381   ATGGTGGAGCATTCCTCGATAAGTTACAAAAACTTTATCCTGAAATCTTCACAAAGAAGC
1030    Y  G  G  A  F  L  D  K  L  Q  K  L  Y  P  E  I  F  T  K  K

4441   AAGTTTCAACTGGTGTTGCTATTGATCCTTCACAAAAGATAACTGAATGGTCAGCAAAAT
1050    Q  V  S  T  G  V  A  I  D  P  S  Q  K  I  T  E  W  S  A  K

4501   ACTTTAATGGAACAAACATTCTCCATCGTGGTTCTGGTTATGTACTAAAAGCTGATGGTG
1070    Y  F  N  G  T  N  I  L  H  R  G  S  G  Y  V  L  K  A  D  G

4561   GTCAATACTACAACTTAGGTACTACTACAAAGCAATTCTTGCCAATTCAATTAACTGGTG
1090    G  Q  Y  Y  N  L  G  T  T  T  K  Q  F  L  P  I  Q  L  T  G

4621   AAAAGAAACAAGGAAATGAAGGCTTTGTTAAGGGTAATGATGGAAATTACTACTTCTATG
1110    E  K  K  Q  G  N  E  G  F  V  K  G  N  D  G  N  Y  Y  F  Y

4681   ACTTAGCAGGTAATATGGTTAAGAATACCTTTATTGAAGATAGTGTTGGCAACTGGTACT
1130    D  L  A  G  N  M  V  K  N  T  F  I  E  D  S  V  G  N  W  Y

4741   TCTTTGACCAAGATGGTAAGATGGTTGAAAATAAACATTTCGTTGATGTTGATTCTTATG
1150    F  F  D  Q  D  G  K  M  V  E  N  K  H  F  V  D  V  D  S  Y

4801   GTGAAAAAGGTACTTACTTCTTCTTGAAGAATGGTGTATCATTCCGTGGGGGATTAGTGC
1170    G  E  K  G  T  Y  F  F  L  K  N  G  V  S  F  R  G  G  L  V

4861   AAACTGACAATGGTACTTATTACTTTGATAATTATGGAAAGATGGTACGTAATCAAACTA
1190    Q  T  D  N  G  T  Y  Y  F  D  N  Y  G  K  M  V  R  N  Q  T

4921   TTAATGCAGGTGCCATGATTTATACCTTAGATGAAAACGGTAAGCTTATAAAGGCTAGTT
1210    I  N  A  G  A  M  I  Y  T  L  D  E  N  G  K  L  I  K  A  S

4981   ATAATTCAGATGCCGAATATCCAACTTCAACTGATGTTGGTAAGATGCTTGATCAAAATA
1230    Y  N  S  D  A  E  Y  P  T  S  T  D  V  G  K  M  L  D  Q  N

5041   AACTATAATTAGCTGATTTCCGTTTCTTAGAATCGAAAGATTTAATAACTGGGGTTAAAA
1250    K  L  *
```

Fig.3G

```
5101    CGGCCCTACAAAATCTGATATTGATATAGAGATATTATTTCCTATATCAATATCAGATTT
        ------------------------>    <------------------------

5161    TTGCTTTTTATAAAATTGATTGTGACTAATAAGAATCCGGAAGATAACGTTGTTGTTATA

5221    TCAGTGGATTTAAGCAACATGAATTAATTGAAGATGACGGCAATGATTAAAAGTCGGTCT

5281    GATGATTATTGATGTATTACTAGTATTTGGTTTTTATCATTTATATTTTTACTGTTATTG

5341    GTGTCATATATTCCACAATAACAGTAAAGGTATATATGCTAGTTTATTTTTTAAGTAATT

5401    ATAATATTCTGATTATAATTTGGAAATATTCGCTTTTAGCAAAAAGGTAGTAAACAGATC

5461    AGAATCGTCATTCTGCTTTTCTACTACTAAAAGTCTGTTTTAAATTCTAAACTAAAATAG

5521    GCTAAACACTGATGTTTATCATTTATATTTTTACTGTT
```

Fig.4A

```
(SEQ ID NO:4) •                          ◊ ⇓  ▽▽
GTFD  LLANDIDNSNPVVQAEQLNWLHYLMNYGSIVANDPEANFDGVRVDAVDNVNADLLQIASD  480
      (SEQ ID NO:5)
DSRS  LLANDVDNSNVVVEAEQLNWLYYLMNFGTITANDADANFDGIRVDAVDNVDADLLQIAAD  576
      (SEQ ID NO:6)
ASR   LLANDIDNSNPIVQAEQLNWLHYLMNFGSITGNNDNANFDGIRVDAVDNVDADLLKIAGD  650
      (SEQ ID NO:7)
GTFA  LLANDIDNSNPVVQAEQLNWLYYLLNFGTITANNDQANFDSVRVDAPDNIDADIMNIAQD  509
      *****.****.*.*******.**.*.*.*   *   ****.****.**.***..**.*

AS    262QWDLN266 (SEQ ID NO:8)             .290IVRMDAVAFI298 (SEQ ID NO:9)
           -------H3------                    --E4-    -----H4--

⇓▽▽▽
GTFD  YLKAHYGVDKSEKNAINELSILEAWSDNDPQYNKDTKGAQLPIDNKLRLSLLYALTRPLE  540
DSRS  YFKLAYGVDQNDATANQHLSILEDWSHNDPLYVTDQGSNQLTMDDYVHTQLIWSLTK--S  634
ASR   YFKALYGTDKSDANANKHLSILEDWNGKDPQYVNQQGNAQLTMDYTVTSQFGNSLTHGAN  710
GTFA  YFNAAYGMD-SDAVSNKHINILEDWNHADPEYFNKIGNPQLTMDDTIK----NSLNHGLS  564
      *  ** *  .   , *.*** *  ** *       ** .*  ,     .*..
      ----             -E5--           ---H5----        ---E6--

GTFD  KDASNKNEIRSGLEPVITNSLN----------------------NRSAEGKNSERMANYIFIRA  582
DSRS  ---SD---IRGTMQRFVDYYMV--------------------DRSNDSTENEAIPNYSFVRA  660
ASR   N-RSN----MWYFLDTGYYLNGDLNKKIVDKNRPNSGTLVNRIANSGDTKVIPNYSFVRA  765
GTFA  D-ATN----RWGLDAIVHQS--------------------LADRENNSTENVVIPNYSFVRA  601
                                       *        .** *.**
AS                                                     396FVRS
       --------------H6-------------                    --E7--
```

Fig.4B

```
            ◆⇓
GTFD  HDSEVQTVIAKIIKAQINPKTDGLTFTLDELKQAFKIYNEDM--RQAKKKYTQSNIPTAY   640
DSRS  HDSEVQTVIAQIVSDLYPDVENSLAPTTEQLAAAFKVYNEDE--KLADKKYTQYNMASAY   718
ASR   HDYDAQDPIRKAMIDHGIIKNMQDTFTFDQLAQGMEFYYKDQENPSGFKKYNDYNLPSAY   825
GTFA  HDNNSQDQIQNAIRDVTGKD--YHTFTFEDEQKGIDAYIQDQ-N-STVKKYNLYNIPASY   657
      **   *  *              *          *  *   *** *   *
AS    HD₁₀₁  (SEQ ID NO:10)
                                                          ----H7-

GTFD  ALMLSNKDSITRLYYGDMYSDDGQYMATKSPYYDAIDTLLKARIKYAAGGQDMKITYVEG   700
DSRS  AMLLTNKDTVPRVYYGDLYTDDGQYMATKSPYYDAINTLLKARVQYVAGGQ--------   769
ASR   AMLLTNKDTVPRVYYGDMYLEGGQYMEKGTIYNPVISALLKARIKYVSGGQTMATDSSGK   885
GTFA  AILLTNKDTIPRVYYGDLYTDGGQYMEHQTRYYDTLTNLLKSRVKYVAGGQSMQTMSVG-   716
      *  * ***  * ****  *    ****     *    ***  * **  *
AS         ₄₈₈GLPRIYLGD₄₉₆ (SEQ ID NO:11)
      H7-       --E8-               --------H8-------

GTFD  DKSHMDWDYTGVLTSVRYGTGANEATDQGSEATK----TQGMAVITSNNPSLKLNQNDKV   756
DSRS  ---SMSVDSNDVLTSVRYGKDAMTASDTGTSETR----TEGIGVIVSNNAELQLEDGHTV   822
ASR   DL---KDGETDLLTSVRFGKGIMTSDQTTTQDNSQDYKNQGIGVIVGNNPDLKLNNDKTI   942
GTFA  ------GNNNILTSVRYGKGAMTATDTGTDETR----TQGIGVVVSNTPNLKLGVNDKV   765
            . *****  *             .     . *  *  *  *  *

GTFD  IVNMGAAHKNQEYRPLLLTTKDGLTSYTSDAAAKSLYRKTND-----------K-GELVFD  805
DSRS  TLHMGAAHKNQAYRALLSTTADGLAYYDTDENAPVAYTDAN-----------GDLIFT   869
ASR   TLHMGKAHKNQLYRALVLSNDSGIDVYDSDDKAPTLRTNDNGDLIFHKTNTFVKQDGTII  1002
GTFA  VLHMGAAHKNQQYRAAVLTTTDGVINYTSDQGAPVAMTDENGDLYLSSHNLVVNGK-EEA   824
       ** ***** **    .   *   *  *  *        *
```

Fig.4C

```
GTFD  ASDIQGYLNPQVSGYLAVWVPVGASDNQDVRVAASNKANATG-QVYESSSALDSQLIYEG   864
DSRS  NESIYGVQNPQVSGYLAVWVPVGAQQDQDARTASDTTTNTSD-KVFHSNAALDSQVIYEG   928
ASR   NYEMKGSLNALISGYLGVWVPVGASDSQDARTVATESSSSNDGSVFHSNAALDSNVIYEG  1062
GTFA  DTAVQGYANPDVSGYLAVWVPVGASDNQDARTAPSTEKNSGN-SAYRTNAAFDSNVIFEA   883
       . *  *  .**** ******  ** *           . ...* **..*.*
                                                          -E1-

GTFD  FSNFQDFVTKDSDYTNKKIAQNVQLFKSWGVTSFEMAPQYVSSEDG-----SFLDSIIQN   919
DSRS  FSNFQAFATDSSEYTNVVIAQNADQFKQWGVTSFQLAPQYRSSTDT-----SFLDSIIQN   983
ASR   FSNFQAMPTSPEQSTNVVIATKANLFKELGITSFELAPQYRSSGDTNYGGMSFLDSFLNN  1122
GTFA  FSNFVYTPTKESERANVRIAQNADFFASLGFTSFEMAPQYNSSKDR-----TFLDSTIDN   938
      ****   .    .* **   *   * ***..**** ** *     .****  *
AS                         134GLTYLHLMP142 (SEQ ID NO:12)
            ---H1--          --E2-

♦
GTFD  GYAFEDRYDLAMSKN--N----KYGSQQDMINAVKALHKSGIQVIADWVPDQ   965
DSRS  GYAFTDRYDLGYGTP--T----KYGTADQLRDAIKALHASGIQAIADWVPDQ  1029
ASR   GYAFTDRYDLGFNKADGNPNPTKYGTDQDLRNAIEALHKNGMQAIADWVPDQ  1174
GTFA  GYAFTDRYDLGMSEP--N----KYGTDEDLRNAIQALHKAGLQVMADWVPDQ   984
      **** *****       ***.  . *. ***  *.* .*******
AS                                190DFITNH195 (SEQ ID NO:13)
       -------H2-------  ---E3--
```

GLUCAN INCORPORATING 4-, 6-, AND 4, 6- LINKED ANHYDROGLUCOSE UNITS

The present invention is in the field of enzymatic production of biomolecules. The invention is particularly concerned with a novel type of glucosyltransferase derived from lactobacilli and with a process for production of the enzyme and for the production of useful glucans and glucooligosaccharides from sucrose. Furthermore, the invention pertains to the produced glucans and glucooligosaccharides.

BACKGROUND OF THE INVENTION

Lactic acid bacteria (LAB) play an important role in the fermentative production of food and feed. Traditionally, these bacteria have been used for the production of for instance wine, beer, bread, cheese and yoghurt, and for the preservation of food and feed, e.g. olives, pickles, sausages, sauerkraut and silage. Because of these traditional applications, lactic acid bacteria are food-grade microorganisms that posses the Generally Recognised As Safe (GRAS) status. Due to the different products which are formed during fermentation with lactic acid bacteria, these bacteria contribute positively to the taste, smell and preservation of the final product. The group of lactic acid bacteria encloses several genera such as *Lactobacillus, Leuconostoc, Pediococcus, Streptococcus,* etc.

In recent years also the health promoting properties of lactic acid bacteria have received much attention. They produce an abundant variety of exopolysaccharides (EPS's). These polysaccharides are thought to contribute to human health by acting as prebiotic substrates, nutraceuticals, cholesterol lowering agents or immunomodulants. To date high molecular weight polysaccharides produced by plants (such as cellulose, starch and pectin), seaweeds (such as alginate and carrageenan) and bacteria (such as alginate, gellan and xanthan) are used in several industrial applications as viscosifying stabilising, emulsifying, gelling or water binding agents. Although all these polysaccharides are used as food additives, they originate from organisms not having the GRAS status. Thus they are less desirable than the exopolysaccharides of microorganisms, such as lactic acid bacteria, which have the GRAS status. The exopolysaccharides produced by lactic acid bacteria can be divided in two groups, heteropolysaccharides and homopolysaccharides; these are synthesized by totally different mechanisms. The former consist of repeating units in which residues of different types of sugars are present and the latter consist of one type of monosaccharide. The synthesis of heteropolysaccharides by lactic acid bacteria, including lactobacilli, has been studied extensively in recent years. Considerable less information is present on the synthesis of homopolysaccharides from lactobacilli, although some studies have been performed. The information on the synthesis of homopolysaccharides in lactobacilli is mainly limited to the synthesis of glucans and only two reports, written by the present inventors, exist on the synthesis of fructans. In one of these reports the *Lactobacillus reuteri* strain LB 121 was found to produce both a glucan and a fructan when grown on sucrose, but only a fructan when grown on raffinose (van Geel-Schutten, G. H. et al., *Appl. Microbiol, Biotechnol.* (1998) 50, 697–703). In the other report was found that *Lactobacillus reuteri* strain LB 35–5, a spontaneous mutant of *Lactobacillus reuteri* strain LB 121, only produced a glucan when grown on sucrose (van Geel-Schutten, G. H. et al., *Appl. Environ. Microbiol.* (1999) 65, 3008–3014). In the other report the soluble glucan and fructan were also characterised by their molecular weights (of 3,500 and 150 kDa respectively) and the glucan was reported to be highly branched with a unique structure consisting of a terminal, 4-substituted, 6-substituted, and 4,6-disubstituted α-glucose in a molar ratio 1.1:2.7:1.5:1.0 (van Geel-Schutten, G. H. et al., *Appl. Environ, Microbiol.* (1999) 65, 3008–3014). These reports are incorporated herein by reference. No structurally identification of a similar glucan produced by a *Lactobacillus* had been reported before. The fructan was identified as a (2→6)-β-D-fructofuranan (also called a levan). This was the first example of levan synthesis by a *Lactobacillus* species.

SUMMARY OF THE INVENTION

A novel enzyme having glucosyltransferase activity using sucrose as a substrate has now been found in *Lactobacillus reuteri*, and its amino acid sequence and other structural properties have been determined. The enzyme is unique in that it is capable of producing a highly branched glucan with α-1,4- and α-1,6 glucosidic links. The invention thus pertains to an enzyme, to DNA encoding it, to cells containing such DNA and to their use in producing carbohydrates, as defined in the appending claims. The invention also pertains to glucans, oligosaccharides and chemically derivatised glucans, containing the unique structure mentioned above.

DESCRIPTION OF THE INVENTION

It was found according to the invention that the glucans are produced by certain *Lactobacillus strains*, in particular by certain strains of *Lactobacillus reuteri*, as a result of the activity of a single glucosyltransferase (glucansucrase).

The nucleotide and amino acid sequences of the novel glucosyltransferase are shown in FIG. 3. As mentioned above, the nucleotide sequence contains two putative start condons leading to either a 3834 or a 3753 nucleotide form of the glucosyltransferase. Both putative start codons are preceded by a putative ribosome binding site, GCAGG (located 4 base pairs upstream its start codon) or AGAAG (located 14 base pairs upstream its start codon), respectively.

This glucosyltransferase consists of either 1278 amino acids (3834 nucleotides) or 1251 amino acids (3753 nucleotides) depending on the potential start codon used. The molecular weight (MW) deduced of the amino acid sequences of these forms is 143 or 140 kDa, respectively. The molecular weight indicated by SDS-PAGE is 180 kDa. The isoelectric point deduced of the amino acid sequence is 4.73 (for the higher MW protein) or 4.71 (for the lower MW protein), at pH 7.

The present invention covers a protein having glucosyltransferase activity with sucrose as substrate with an amino acid identify of at least 50%, preferably at least 60%, and more preferably at least 70%, compared to the amino acid sequence of SEG ID No. 1. The invention also covers a part of a protein with at least 15 contiguous amino acids which are identical to the corresponding part of the amino acid sequence of SEQ ID No. 1. The novel glucosyltransferase has homology with several other proteins as revealed by amino acid sequence alignment. A high homology (FIG. 5) was found with an alternansucrase of *Leuconostoc mesenteroides* strain NRRL B-1355 (46% identity, within 1261 amino acids) and a dextransucrase of *Leuconostoc mesenteroides* strain NRRL B-512F (44% identity, within 1270 amino acids). Furthermore, the alignment revealed the presence of various domains also found in the other glucosyltransferases, such as an N-terminal variable domain, a catalytic domain and a C-terminal glucan binding domain. The N-terminal domain shows almost no identity with the N-terminal domains of other glucosyltransferases and an N-terminal signal peptide could not be detected.

The invention also covers a protein comprising an amino acid sequence of at least 100 amino acids, exhibiting at least 55%, preferably at least 65% amino acid identity with the corresponding part of the amino acid sequence 442–984 (catalytic domain) of SEQ ID No. 1. The catalytic domain shows a high level of homology (about 50% identity) with other known *streptcoccal* and *Leuconostoc* glucosyltransferases and putative functions based on the alignment can be ascribed to several amino acids within this catalytic domain (FIG. 4). Asp-494, Glu-531 and Asp-603 are putative catalytic residues, Asp-454 is a putative calcium binding residue and Arg-492 a putative chloride binding residue. His-602 and Gln-984 may stabilize the transition state and the residues Asp-497, Asn-498, Asp-532 and Trp-533 may play a role in binding of acceptor molecules and in the transfer of the glucosyl moiety.

The invention further covers a protein comprising an amino acid sequence of at least 100 amino acids, exhibiting at least 50%, preferably at least 60%, amino acid identity with the corresponding part of the amino acid sequence 985–1251 (glucan binding domain) of SEQ ID No. 1. The C-terminal putative glucan binding domain is much shorter than the corresponding domains in other glucosyltransferases but three known repeats, resembling YG agents, are described: (piece of SEQ ID NO:3) YYFYDLAGNMVKN starting at position 1126, (piece of SEQ ID NO:3) WYFFDQDGKMVEN starting at position 1148 (piece of SEQ ID NO:3) and TYYFDNYGKMVRN starting at position 1195. YG repeats are defined by the presence of one or more aromatic residues (of which one is usually tyrosine), followed by 3–4 glycine residues downstream a hydrophobic residue, a neutral polar residue (usually glycine or asparagine) and 1–3 hydrophobic residues. It is striking that the number of repeats necessary to ensure glucan binding properties is different for enzymes producing a soluble or an insoluble glucan. Possibly the glucan binding domain is also involved in the determination of the glucan structure and the polymer chain growth. Furthermore, this domain seems also necessary for the complete glucosyltransferase activity.

Specific amino acids of the glucosyltransferase that are believed to be important for the unique properties of the enzyme Pro-496, Ile-499, Met-504, Asn-505, Ser-606, Ala-613, Ile-640, Leu-693, Ala-883, Val-888, Ala-898, Leu-912 of the amino acid sequence of SEQ ID No. 1. So a protein, mutant or part thereof, comprising at least one of the above mentioned amino acids is also part of the invention. Particularly Pro-496 and Ile-499 are of interest. Pro-496 is found where a conserved Val is found in other glucosyltransferases. Compared with Val, the presence of Pro results in a more rigid protein structure. This change of protein structure might influence the glucosidic bonds formed and might explain the unique structure of the glucan. Ile-499 is also found in a position where a conserved Val is present in other LAB glucosyltransferases not producing α(1,4) bonds. An identical amino acid substitution is observed in amylosucrase, a glucosyltransferase synthesizing α(1,4) bonds.

A nucleotide sequence encoding any of the above mentioned proteins, mutants, variants or parts thereof is also a subject of the invention. Furthermore, the nucleic acid sequences corresponding to expression-regulating regions (promoters, enhancers, terminators) contained in the nucleic acid sequence (-221)-(-1) or 5050–5559 of FIG. 3 can be used for homologous or heterologous expression of genes. Such expression-regulating sequences are operationally linked to a polypeptide-encoding nucleic acid sequence such as the genes of the glucosyltransferase according to the invention. Inverted repeats are located 62 base pairs downstream the termination codon (AAT), suggesting the presence of a Rho independent transcription termination signal. The -10 and -35 consensus promoter sequences, two motifs generally present upstream of the start codon of procaryotes, could not be identified. Other promoter, enhancer or terminator were also not identified. A nucleic acid construct comprising the nucleotide sequence operationally linked to an expression-regulating nucleic acid sequence is also covered by the invention.

A recombinant host cell, such as a mammalian (with the exception of human), plant, animal, fungal or bacterial cell, containing one or more copies of the nucleic acid construct mentioned above is an additional subject of the invention. The glucosyltransferase gene has been cloned and expressed in *E. coli*. The molecular weight predicted from the deduced amino acid sequence of the recombinant glucansucrase expressed in *E. coli* is 145 kDa.

The invention further covers a protein according to the invention which, in the presence of sucrose, produces a glucan having 38–48% 4-linked anhydroglucose units, 17–28% 6-linked anhydroglucose units, and 7–20% 4,6-linked anhydroglucose units, preferably a glucan having 40–46% 4-linked anhydroglucose units, 19–26% 6-linked anhydroglucose units, and 9–18% 4,6-linked anhydroglucose units. There is a large variation in glucans due to differences in the type of bonds present, degree and type of branching, length of the glucan chains, molecular weight, and the conformation of the polymers. The structure of this glucan is unique in that it is highly branched, consists of terminal, 4-substituted, 6-substituted, and 4,6-disubstituted α-glucose in a molar ratio 1.1:2.7:1.5:1.0 and has a high molecular weight of 3500 kDa. The novel glucan may be synthesized by a glucosyltransferase present in the *Lactobacillus* strains, preferably *Lactobacillus reuteri* strains and more preferably *Lactobacillus reuteri* strains LB 121 and LB 35–5. The glucosyltransferase is synthesized during growth on various sugars and occurs in a cell-bound state and in a cell-free state in sucrose and maltose cultures, but only in a cell-bound state in glucose cultures. *Lactobacillus reuteri* belongs to the group of lactic acid bacteria which are known to play an important role in the fermentative production of food and feed. Because of this, lactic acid bacteria are food-grade micro-organisms that posses the Generally Recognised As Safe (GRAS) status.

The invention also pertains to a process of producing a glucan as described above. This glucan can be produced by a *Lactobacillus* strain, preferably a *Lactobacillus reuteri* strain, and more preferably *Lactobacillus* strain LB 121 or LB 35–5 or by an isolated glucosyltransferase according to the invention and a suitable glucose source such as for instance sucrose. The glucosyltransferase may be isolated by conventional means from the culture of a glucosyltransferase-positive lactic acid bacterium, especially a *Lactobacillus reuteri*, or from a recombinant organism expressing the glucosyltransferase gene.

Additionally, the invention concerns a process of producing gluco-oligosaccharides containing the characteristic structure of the glucan described above using an isolated glucosyltransferase according to the invention or a *Lactobacillus* strain, preferably a *Lactobacillus reuteri* strain, containing a glucosyltransferase according to the invention. There is a growing interest in oligosaccharides derived from homopolysaccharides, for instance for prebiotic purposes.

Several fructo- and gluco-oligosaccharides are known to stimulate the growth of bifidobacteria in the human colon. Gluco-oligosaccharides produced by the glucosyltransferase described above can be used as prebiotics and probiotics and are also part of the invention. The production of the gluco-oligosaccharides is different from the glucan synthesis reaction. In addition to sucrose, the substrate of the glucosyltransferase, an acceptor molecule such as maltose or lactose is necessary for the acceptor reaction. Another way of producing gluco-oligosaccharides is by hydrolysis of the glucan described above. This hydrolysis can be performed by known hydrolysis methods such as enzymatic hydrolysis with enzymes such as amylase, dextranase or pullulanase or by acid hydrolysis. The produced gluco-oligosaccharides must contain at least one 1,6-glucosidic link to be used as prebiotics, for improving the bacterial status in the mammalian, especially human colon.

The invention also covers a glucan having 38–48% 4-linked anhydrogulcose units, 17–28% 6-linked anhydroglucose units, and 7–20% 4,6-linked (branching) anhydroglucose units, preferably a glucan having 40–46% 4-linked anhydroglucose units, 19–26% 6-linked anhydroglucose units, and 9–18% 4,6-linked anhydroglucose units and a gluco-oligosaccharide containing at least two 4-linked anhydroglucose units, at least one 6-linked anhydroglucose units and at least one 4,6-double linked anhydroglucose units. The novel gluco-oligosaccharides contain at least 5, preferably at least 6 or even at least 8 anhydroglucose units. In addition, they may contain one non-glucose terminal unit such as galactose, mannose or fructose. The glucan and the gluco-oligosaccharides described above can be recovered from the culture supernatant of $Lactobacillus$ strains, preferably $Lactobacillus$ $reuteri$ strains, and more preferably $Lactobacillus$ $reuteri$ strains LB 121 and LB 35–5, containing the glucosyltransferase according to the invention. The glucan can comprise at least 20, up to 100,000 α-anhydroglucose units with the unique structure described above. The molecular mass of the glucan synthesized by the $Lactobacillus$ strains $LB$ 121 and LB 35–5 was 3,500 kDa.

The invention also concerns chemically modified glucans and gluco-oligosaccharides based on the 1,4/1,6-α-glucans described above. Chemical modification can be achieved by oxidation, such as hypochlorite oxidation resulting in ring-opened 2,3-dicarboxy-anhydroglucose units (see e.g. EP-A-427349), periodate oxidation resulting in ring-opened 2,3-dialdehyde-anhydroglucose units (see e.g. WO95/12619), which can be further oxidised to (partly) carboxylated units (see e.g. WO 00/26257), TEMPO-mediated oxidation resulting in 6-carboxy-anhydroglucose units (see e.g. WO 95/07303). The oxidised glucans have improved water-solubility, altered viscosity and a retarded fermentability and can be used as metal-complexing agents, detergent additives, strengthening additives, bioactive carbohydrates, emulsifiers and water binding agents. They can also be used as starting materials for further derivatisation such as cross-linking and the introduction of hydrophobes. Oxidised glucans coupled to proteins can be used as emulsifiers and stabilizers. (Partial) hydrolysis of said glucans would result in gluco-oligosaccharides, which can be used as bioactive carbohydrates or prebiotics.

Another type of chemical modification is phosphorylation, as described in O. B. Wurzburg (1986) Modified Starches: properties and uses. CRC Press Inc. Boca Raton, 97–112. One way to achieve this modification is by dry heating glucans with a mixture of monosodium and disodium hydrogen phosphate or with tripolyphosphate. The phosphorylated glucans are suitable as wet-end additives in papermaking, as binders in paper coating compositions, as warp sizing-agents, and as core binders for sand molds for metal casting. A further type of derivatisation of the glucans is acylation, especially acetylation using acetic or propionic anhydride, resulting in products suitable as bleaching assistants and for the use in foils. Acylation with e.g. alkenyl succinic anhydrides or (activated) fatty acids results in surface-active products suitable as e.g. surfactants, emulsifiers, and stabilizers.

Hydroxyalkylation, carboxymethylation, and aminoalkylation are other methods of chemical derivatisation of the glucans. Hydroxyalkylation is commonly performed by base-catalysed reaction with alkylene oxides, such as ethylene oxide, propylene oxide or epichlorohydrine; the hydroxyalkylated products have improved solubility and viscosity characteristics. Carboxymethylation is achieved by reaction of the glucans with mono-chloroacetic acid or its alkali metal salts and results in anionic polymers suitable for various purposes including crystallisation inhibitors, and metal complexants. Amino-alkylation can be achieved by reaction of the glucans with alkylene imines, haloalkyl amines or amino-alkylene oxides, or by reaction of epichlorohydrine adducts of the glucans with suitable amines. These products can be used as cationic polymers in a variety of applications, especially as a wet-end additive in paper making to increase strength, for filler and fines retention, and to improve the drainage rate of paper pulp. Other potential applications include textile sizing and wastewater purification. The above mentioned modifications can be used either separately or in combination depending on the desired product. Furthermore, the degree of chemical modification is variable and depends on the intended use. If necessary 100% modification, i.e. modification of all anhydroglucose units can be performed. However, partial modification, e.g. from 1 modified anhydroglucose unit per 100 up to higher levels, will often be sufficient in order to obtain the desired effect.

Use of a $Lactobacillus$ strain capable of producing the novel and unique glucan is also covered by the invention. Preferably, the strain is also capable of producing a fructan, which can be either a levan, inulin or both. More preferably, the strain is also capable of producing fructo-oligosaccharides. The efficacy of some $Lactobacillus$ $reuteri$ strains as a probiotic has been demonstrated in various animals such as for instance poultry and humans. The administration of $Lactobacillus$ $reuteri$ to pigs resulted in significantly lower serum total and LDL-cholesterol levels, while in children $Lactobacillus$ $reuteri$ is used as a therapeutic agent against acute diarrhea. For this and other reasons $Lactobacillus$ $reuteri$ has already been supplemented to commercially available probiotic products. The mode of action of $Lactobacillus$ $reuteri$ as a probiotic is still unclear. Preliminary studies indicated that gut colonization by $Lactobacillus$ $reuteri$ may be of importance. According to the invention, it was found that the mode of action of $Lactobacillus$ $reuteri$ as a probiotic may reside partly in the ability of produce polysaccharides. $Lactobacillus$ strains, preferably $Lactobacillus$ $reuteri$ strains, more preferably $Lactobacillus$ $reuteri$ strains LB 121, LB 35–5 and other strains capable of producing a glucan having 38–48% 4-linked anhydroglucose units, 17–28% 6-linked anhydroglucose units, and 7–20% 4,6-linked anhydroglucose units, preferably a glucan having 40–60% 4-linked anhydroglucose units, 19–26% 6-linked anhydroglucose units, and 9–18% 4,6-linked anhydroglucose units can thus advantageously be used as a probiotic. They can also, together with these polysaccharides, be used as a symbiotic.

EXAMPLES

Example 1: Isolation of DNA from *Lactobacillus reuteri*, nucleotide sequence analysis of the glucosyltransferase gene, construction of plasmids for expression of the glucosyltransferase gene in *E. coli* DH5α, expression of the glucosyltransferase gene in *E. coli* DH5α and identification of the novel glucan produced by the recombinant enzyme.

General procedures for cloning, DNA manipulations and agarose gel electrophoresis were essentially as described by Sambrook et al. (1989) Molecular cloning: a laboratory manual, 2nd ed. *Cold Spring Harbour Laboratory Press*, Cold Spring Harbour, N.Y. Restriction endonuclease digestions and ligations with T4 DNA ligase were performed as recommended by the suppliers. DNA was amplified by PCR techniques using ampliTAQ DNA polymerase (Perkin Elmer). DNA fragments were isolated from agarose gels using the Qiagen extraction kit (Qiagen GMBH), following the instructions of the suppliers. *Lactobacillus reuteri* strains were grown anaerobically at 37° C. in MRS medium (DIFCO) or in MRS-s medium (MRS medium containing 100 g/l sucrose instead of 20 g/l glucose) and *E. coli* strains were grown aerobically at 37° C. in LB medium containing 100 μg/l ampicillin (when appropriate 40 μg/ml X-gal was added).

For the isolation of chromosomal DNA, *Lactobacillus reuteri* 121 was grown overnight at 37° C. in MRS both (Difco) supplemented with 40 mM DL-threonine. Cells of 4 ml culture were harvested by centrifugation and resuspended in 10 ml MRS both supplemented with 40 mM DL-threonine and incubated for 2 h at 37° C. After centrifugation the cells were resuspended in 400 μl protoplast buffer (10 mM sodium maleate, pH 6.1 supplemented with 0.3 M lactose, 10 mM MgCl$_2$, 12% polyethyleneglycol 2000, 0.1 M EDTA, 5 mg/ml lysozyme (47,000 U/mg) and 10 U/ml mutanolysine) and incubated for 1 h at 37° C. After centrifugation (1 min, Eppendorf centrifuge), protoplasts were resuspended in 500 μl 20 mM Tris-HCl, pH 8.0. Subsequently, 100 μl laurylsarcosine and 150 μl 5 M NaCl were added and DNA was extracted. Plasmid DNA of *Lactobacillus reuteri* was isolated using a modification of the methods of Anderson and Mc Kay (1983) *Appl. Environ. Microbiol.* 46, 549–552 and Burger and Dicks (1994) *Biotechnol. Technol.* 8, 769–772. Fresh prewarmed (37° C.) MRS broth (10 ml) was inoculated with 200 μl of an overnight culture and incubated for 2.5 h at 37° C. Cells were harvested by centrifugation and washed with 2 ml sterile STE buffer (0.1 M NaCl, 10 mM Tris-Hcl, 1 mM EDTA, pH 8). After centrifugation, the pellet was resuspended in 380 μl solution I (0.5 M sucrose, 50 mM Tris-HCl, 1 mM EDTA, pH 8, containing 2 mg/ml lysozyme and 6.6 U mutanolysin). After an incubation of 1.5 h at 37° C., 50 μl of solution II (50 mM Tris-HCl, pH 80, 0,25 M EDTA) and 30 μl of solution III (50 mM Tris-HCL, pH 8, 20 mM EDTA, 20% SDS) were added and the suspension was mixed. Sodiumhydroxide (30 μl of a 3 M solution) was added, followed by 50 μl 2 M Tris-HCl and 72 μl 5 N NaCl. After extraction with equal volumes of phenol and chloroform, the DNA was precipitated with ethanol.

The glucosyltransferase (gtfA) gene was identified by amplification with PCR using degenerated primers (GTFpr1 (SEQ ID NO:14, 5' GAYAAKWSIAAKSYIRTIGTI-SARGC3' and GTFpr2 SEQ ID NO: 15, 5' GIKCICA-IATRATRCCICTRIA3'; Y=T or C, K=G or T, W=A or T, S=C or G, R=A or G, I=A, C, G or T) based on conserved amino acid sequences deduced from different glucosyltransferase genes (gtfS of *Streptococcus downei*, gtfC of *S. mutans*, gtfl of *S. downei*, gtfK and gtfM of *S. salivarius* and dsrA of *Leuconostoc mesenteroides*) and *Lactobacillus reuteri* chromosomal DNA as template. An amplification project with the predicted size of about 660 bp was obtained (FIG. 1A). To investigate the possible presence of multiple copies of the glucosyltransferase gene, Southern hybridization was performed. DNA was restricted with endonucleases, separated by agarose gel electrophoresis and transferred to a Hybond nylon membrane. For hybridization probes were labelled with [α–$^{32}$P]dCTP using Random Primed DNA labeling kit (Boehringer Mannheim), following the manufacturer's instructions. The Southern hybridization of chromosomal DNA of the *Lactobacillus reuteri* strain 121 with the amplified 660 bp PCT fragment, followed by washing under non-stringent conditions (45° C. 0.5 x SSC/0.1 SDS) revealed one hybridizing fragment, suggesting the presence of only a single copy of a glucosyltransferase gene in the *Lactobacillus retueri* strains. The 660 bp fragment was cloned in *E. coli* JM109 using the pCR2.1 vector. Transformations were performed by electroporation using the BioRad gene pulser apparatus at 2.5 kV, 25 μF and 200 Ω, following the instructions of the manufacturer. The fragment was sequenced by the method of Sanger et al. (1977) *Proc. Natl. Acad. Sci.* USA 74, 5463–5467, confirming that the correct part of the gtfA gene had been isolated. The 660 bp amplified fragment was used to design primers for inverse PCR. Using inverse PCR techniques a 3 kb fragment of the isolated gtfA gene was generated (FIG. 1B). This 3 kb amplicon was identified by sequencing and probes were designed to isolate the EcoRI/BgIII and EcoRI/HindIII fragments from a partial DNA library of *Lactobacillus reuteri* in *E. coli* DH5α (FIG. 1C). Positive clones were selected by colony blot hybridization using Hybond-N filters, following the instructions of the supplier and the cloned fragments were sequenced. Attempts to clone the C-terminal part of the glucansucrase gene in *E. coli* DH5α or JM109 using a partial DNA library strategy with different vectors failed. Therefore, the C-terminal part was isolated by inverse PCR. The remaining fragment, located between the EcoRI/BglII and EcoRI/HindIII fragments, was isolated by PCR techniques (FIG. 1D). The amplicons obtained were sequenced directly. To eliminate errors due to the PCR reaction, these fragments were sequenced for at least 4 times, using different clones per PCR reaction. Both DNA strands of the entire glucosyltransferase gene were sequenced twice. In this way the sequence of a 5.5 kb region of the *Lactobacillus reuteri* chromosomal DNA, containing the gtfA gene and its surroundings, were obtained.

The plasmids for expression of the glucosyltransferase gene in *E. coli* DH5α were constructed as described hereafter. A 4.8 kb fragment, containing the entire glucosyltransferase gene (ORF1), together with a part of an upstream open reading frame (ORF2) was generated by PCR, using the primers GTFpr3 (SEQ ID NO:16) (5' ACAACCAC-CATGGAATTAGGTCGCACTGATGTAA C3') and GTFpr4 (SEQ ID NO: 17) (5' GCCAGCTGGATC-CGTCGACTAGTTTATTTTTGATC AAGCATCTTACC3'). Both primers contained suitable restriction enzyme recognition sites at their 5' ends (NcoI in GTFpr3 and BamhHI and SalI in GTFpr4). Cloning of this PCR fragment in different vectors failed. Therefore, the strategy depicted in FIG. 2 was followed. Briefly, the PCR product was restricted with XbaI/PstI and PstI/BamHI (FIG. 1; BamHI site was introduced with GTFpr4). The resulting fragments (1503 bp and 2696 bp, respectively) were cloned separately in pBluescriptIISK+yielding PBXP1500 and pBPB2700. Ligation of the 2700 bp PstI/SalI fragment isolated from pBPB2700 in pBXP1500, digested with PstI and SalI, yielded pBGTF (7146 bp) in E. coli DH5α. Plasmid DNA of E. coli was isolated using the alkaline lysis method of Birnboim and Doly (1979) Nucleic. Acid Res. 7, 1513–1523 or with a Qiagen plasmid kit following the instructions of the supplier. Cells of E. Coli DH5α with pBGTF were harvested by centrifugation after 16 h of growth. The pellet was washed with 50 mM sodium acetate buffer pH 5.5 containing 1 mM $CaCl_2$ and 1% (v/v) Tween-80 and the suspension was centrifugation again. Pelleted cells were resuspended in 50 mM sodium acetate buffer pH 5.5 containing 1 mM $CaCl_2$, 1% (v/v) Tween-80 and 7.2 mM β-mercaptoethanol. Cells were broken by sonication. Cells debris and intact cells were removed by centrifugation for 15 min at 4° C. at 14,000 rpm in an Eppendorf centrifuge and the resulting cell free extract was used in the enzyme assays.

The glucosyltransferase activity was determined at 37°C by monitoring the release of frutose from sucrose or by measuring the amount of glucan produced using E. coli cell free extracts or Lactobacillus reuteri culture supernatant in reaction buffer (50 mM sodium acetate, 1 mM $CaCl_2$, 1% (v/v) Tween-80, 10 g/l sucrose, pH 8). Sucrose, glucose and fructose were determined using commercially available kits. For determination of the molecular weight of the glucosyltransferase produced by E. coli or Lactobacillus reuteri, SDS-PAGE was performed according to Laemmli (1970) Nature 227, 680–685. SDS-PAGE gels were stained using the PAS activity staining. Glucans were collected by precipitation with ethanol. $^1$H-NMR spectroscopy (FIG. 6) and methylation analysis (table 1) were perfomed as described by van Geel-Schutten et al. (1999) Appl. Environ. Microbiol. 65, 3008–3014. The molecular weights of the glucans were determined by high performance size exclusion chromotography coupled on-line with a multi angle laser light scattering and a differential refractive index detector.

TABLE 1

Methylation analysis of the glucans produced by Lactobacillus reuteri strains and E. coli GTFA.

| Type of glucosyl units | Lactobacillus reuteri strain 121 | Lactobacillus reuteri strain 35-5 | E. coli GTFA |
|---|---|---|---|
| Glcp-(1 → | 24% | 25% | 21% |
| → 4)-Glcp-(1 → | 42% | 43% | 44% |
| → 6)-Glcp-(1 → | 22% | 21% | 24% |
| → 4,6)-Glcp-1 → | 12% | 11% | 11% |

DESCRIPTION OF THE FIGURES

SEQ ID No. 1: The deduced amino acid sequence of GTFA of Lactobacillus reuteri.

FIG. 2: The general principle of the construction of the recombinant plasmid with the gtfA gene, A PCR product containing the gtfA gene was digested with XbaI and PstI and with PstI and BahHI. The XbaI/PstI (depicted in white) was ligated into the multiple cloning site of pBluescriptIISK+in the same direction relatively to the lacZ promoter, resulting in pBXP1500. The PstI/BamHI part (depicted in grey) was ligated into the multiple cloning site of pBluescriptIISK+in the opposite direction relatively to the lacZ promoter, resulting in pBPB2700. pBXP1500 was used as a vector for subcloning the C-terminal part of the gtfA. pBPB2700 was digested with PstI and SalI and ligated into pBXP1500, also digested with PstI and SalI. The resulting plasmid, pBGTF, contained the entire gtfA in the same direction relative to the lacZ promoter. The sign indicates the restriction.

FIG. 3: The nucleotide and deduced amino acid sequence of gtfA of Lactobacillus reuteri (ORFI) and part of the upstream ORF2. The putative start codons are shown in bold. The underlined nucleotides indicate the putative ribosomal binding sites (rbs). The inverted repeats (transcription termination) are depicted with arrows. The YG repeats in the C-terminal region are shown in bold italics. The sign indicates the stop codon.

FIG. 4: Alignment of catalytic cores of alternansucrase (ASR) of Leuconostoc mesenteroides strain NRRL B-1355 dextransuscrase (DSRS) of Leuconostoc mesenteroides strain NRRL B-512F, glucosyltransferase-D (GTFD) of Streptococcus mutans GS5, glucosyltransferase-A of Lactobacillus reuteri and amylosucrase (AS) of Neisseria polysaccharea. indicates identical or conserved residues in all sequences); , gap in the sequence; AA amino acids which are conserved in all other glucosyltransferases but not in GTFA; , putative catalytic residues; , putative calcium binding sites; ♦, putative residues stabilizing the transition state; ▽, residues possibly playing a role in binding of acceptor molecules and in the transfer of the glucosyl residue; ◊, putative chloride binding sites; -Ex-, localization of β-strands; -Hx-, localization of α-helices according to Mac Gregor et al. (1996) FEBS Let. 378, 262–266.

SEQUENCE LISTING

<160> NUMBER OF SEQ ID NOS: 17

Figure 1:
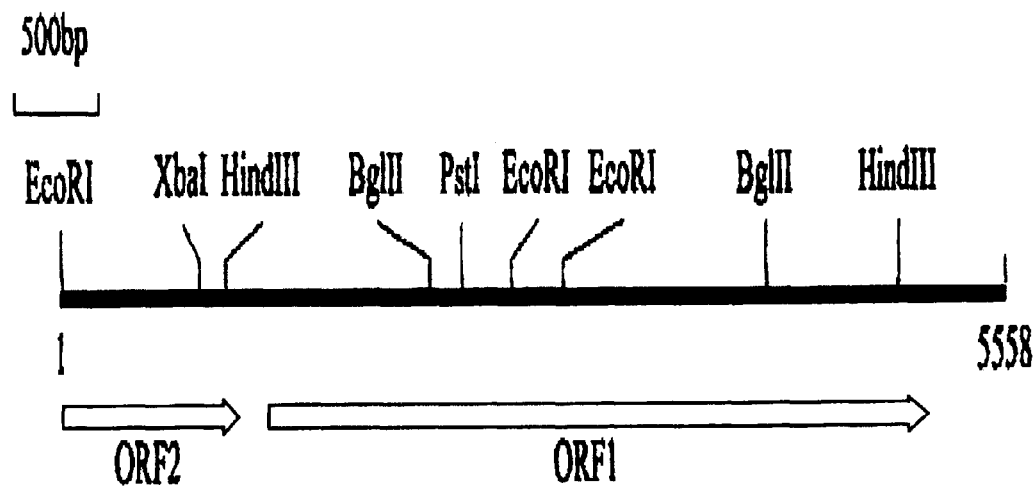
FIG. 1: The strategy used for the isolation of the gtfA gene from Lactobacillus reuteri 121 chromosomal DNA.
Figure 5:
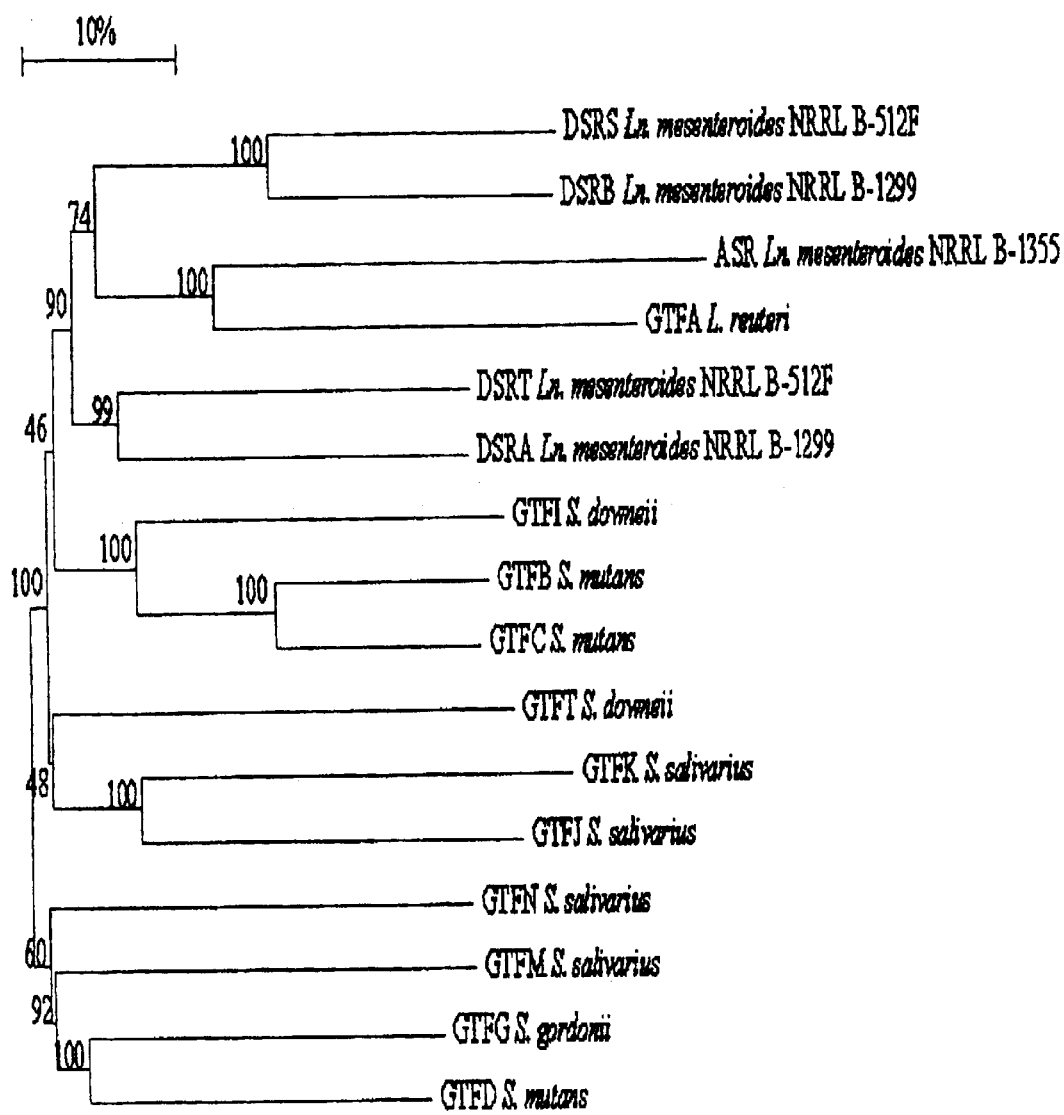
FIG. 5: Dendrogram of glucansucrases of lactic acid bacteria. The horizontal distances are a measure for the difference at the amino acid sequence level. 10% difference is indicated by the upper bar. Bootstrap values (in percentages) are given at the root of each branch.
Figure 6A:
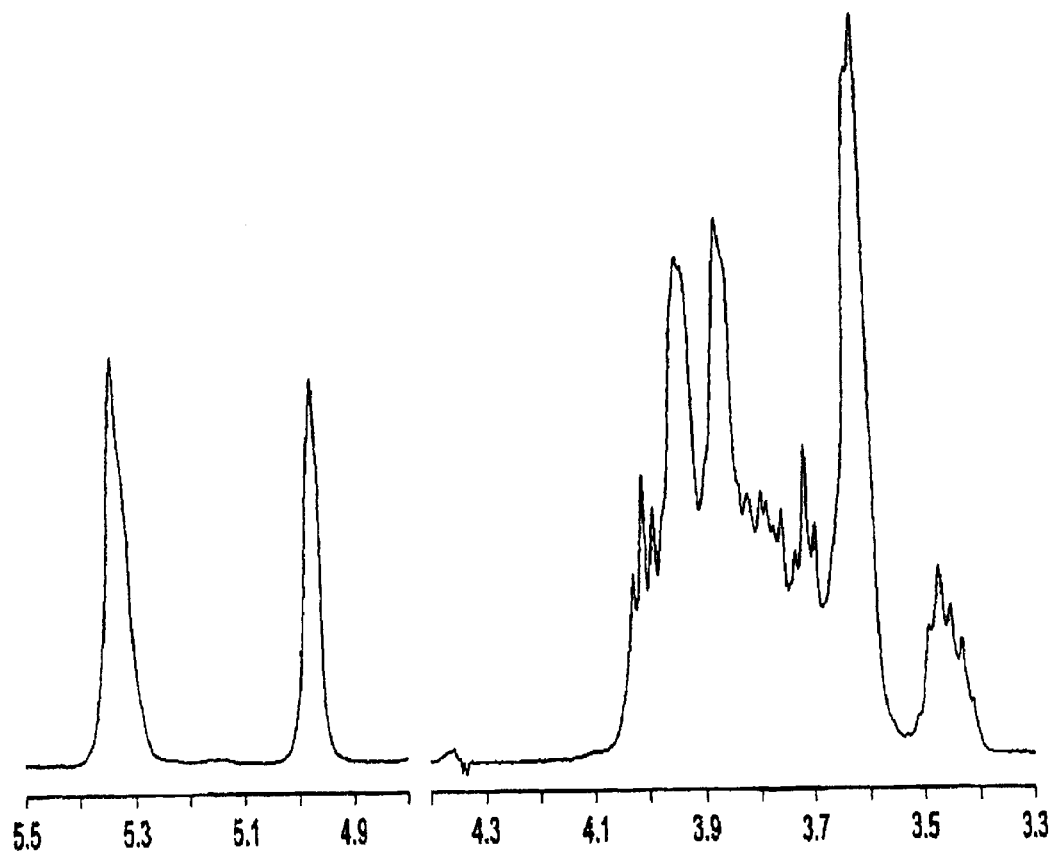
FIG. 6: 500-MHz $^1$H-NMR spectra of the glucan produced by Lactobacillus reuteri GTFA (A) and by E. coli GTFA (B), recorded in $D_2O$ at 80° C.
Figure 6B:
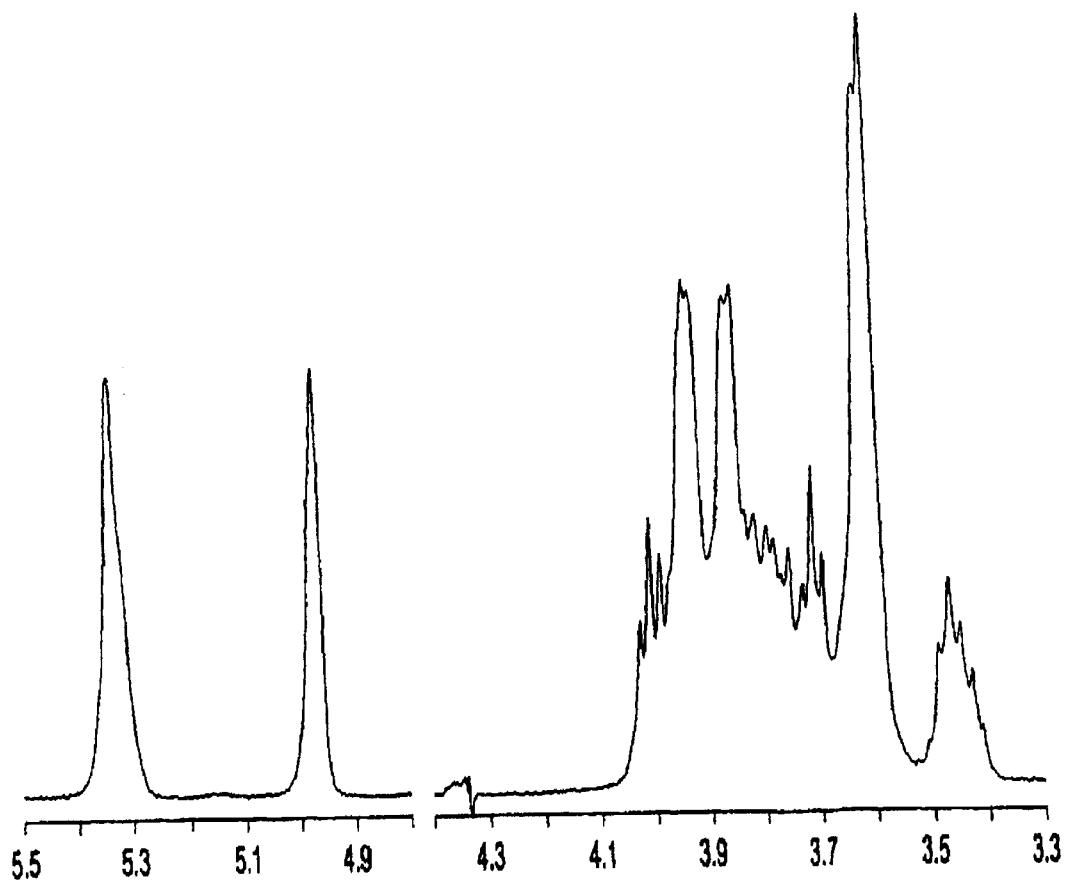

<210> SEQ ID NO 1
<211> LENGTH: 5558
<212> TYPE: DNA

-continued

```
<213> ORGANISM: Lactobacillus reuteri
<220> FEATURE:
<221> NAME/KEY: CDS
<222> LOCATION: (1)..(987)
<221> NAME/KEY: CDS
<222> LOCATION: (1212)..(5045)

<400> SEQUENCE: 1 tct act tct aca cct gtt tct gtt ttg cca tct aat aat act gaa aaa      48
Ser Thr Ser Thr Pro Val Ser Val Leu Pro Ser Asn Asn Thr Glu Lys
 1               5                  10                  15 caa gct aaa aat tat aat gag caa gac aaa gga aac tat ggg aat att      96
Gln Ala Lys Asn Tyr Asn Glu Gln Asp Lys Gly Asn Tyr Gly Asn Ile
            20                  25                  30 gat act gct tac ttt agc aat aat caa ttg cat gtt tca gga tgg aat     144
Asp Thr Ala Tyr Phe Ser Asn Asn Gln Leu His Val Ser Gly Trp Asn
        35                  40                  45 gca acg aac gca tct caa gga aca aac agt cga caa atc att gtg cgt     192
Ala Thr Asn Ala Ser Gln Gly Thr Asn Ser Arg Gln Ile Ile Val Arg
    50                  55                  60 gat atc aca acc aat aat gaa tta ggt cgc act gat gta aca aac aat     240
Asp Ile Thr Thr Asn Asn Glu Leu Gly Arg Thr Asp Val Thr Asn Asn
 65                  70                  75                  80 gtt gca cgc cca gac gtt aag aat gtt cat aat gtt tat aac gct gat     288
Val Ala Arg Pro Asp Val Lys Asn Val His Asn Val Tyr Asn Ala Asp
                 85                  90                  95 aat tct gga ttt gat gtt aat gtc aat att gac ttt agc aag atg aaa     336
Asn Ser Gly Phe Asp Val Asn Val Asn Ile Asp Phe Ser Lys Met Lys
            100                 105                 110 gat tat cgg gat tca att gaa att gtt agt cga tac agt gga aac ggt     384
Asp Tyr Arg Asp Ser Ile Glu Ile Val Ser Arg Tyr Ser Gly Asn Gly
        115                 120                 125 aaa tct gtt gac tgg tgg tcc caa ccg atc act ttt gac aaa aac aac     432
Lys Ser Val Asp Trp Trp Ser Gln Pro Ile Thr Phe Asp Lys Asn Asn
    130                 135                 140 tat gct tat ctt gat aca ttt gaa gtg aaa aat ggc gaa tta cat gca     480
Tyr Ala Tyr Leu Asp Thr Phe Glu Val Lys Asn Gly Glu Leu His Ala
145                 150                 155                 160 acc gga tgg aat gct act aat agt gcg att aac tat aat cac cat ttt     528
Thr Gly Trp Asn Ala Thr Asn Ser Ala Ile Asn Tyr Asn His His Phe
                165                 170                 175 gtg att ttg ttt gat caa acg aat ggt aaa gaa gta gca cga caa gaa     576
Val Ile Leu Phe Asp Gln Thr Asn Gly Lys Glu Val Ala Arg Gln Glu
            180                 185                 190 gtt cgt gaa ggt caa tca cgc cca gat gtt gct aag gta tat cca caa     624
Val Arg Glu Gly Gln Ser Arg Pro Asp Val Ala Lys Val Tyr Pro Gln
        195                 200                 205 gta gtt ggt gct gcc aac tca ggc ttt aat gtg aca ttt aat atc agt     672
Val Val Gly Ala Ala Asn Ser Gly Phe Asn Val Thr Phe Asn Ile Ser
    210                 215                 220 gat tta gat tat act cac cag tac caa gtt ctt agt cgt tac agc aat     720
Asp Leu Asp Tyr Thr His Gln Tyr Gln Val Leu Ser Arg Tyr Ser Asn
225                 230                 235                 240 tct gat aat ggc gaa ggt gat aac gtt acc tac tgg ttt aat cca caa     768
Ser Asp Asn Gly Glu Gly Asp Asn Val Thr Tyr Trp Phe Asn Pro Gln
                245                 250                 255 tcc att gct cct gct aat caa agt aac cag ggt tat cta gac tca ttt     816
Ser Ile Ala Pro Ala Asn Gln Ser Asn Gln Gly Tyr Leu Asp Ser Phe
            260                 265                 270 gat att agt aaa aat ggt gaa gta aca gta act gga tgg aac gct act     864
Asp Ile Ser Lys Asn Gly Glu Val Thr Val Thr Gly Trp Asn Ala Thr
```

-continued

```
                 275                 280                 285
gac ttg tca gaa tta caa aac aac cat tat gtg att cta ttt gat cag       912
Asp Leu Ser Glu Leu Gln Asn Asn His Tyr Val Ile Leu Phe Asp Gln
290                 295                 300 aca gca ggc aaa caa gtt gca tct gct aaa gct gat tta att tca cgt       960
Thr Ala Gly Lys Gln Val Ala Ser Ala Lys Ala Asp Leu Ile Ser Arg
305                 310                 315                 320 cca gat gtt gct aaa gct tat cca cag taaaaacagc tacaaattct            1007
Pro Asp Val Ala Lys Ala Tyr Pro Gln
                325 ggcttcaagg taacatttaa ggttaataac ttacaaccgg gtcaccaata cagcgttgta    1067 agtcgtttct ctgccgatga aaatggtaat ggtaatgata agcgccatac agattactgg    1127 tttagtccag taatattaaa ccagactgct tcaaacattg atactattac aatgacatct    1187 aatggtttac atattgcagg ttgg atg gca agt gat aac tca att aat gaa       1238
                          Met Ala Ser Asp Asn Ser Ile Asn Glu
                          330                 335 aca act cca tac gct att atc ctc aat aat gga aaa gaa gtt act cgt      1286
Thr Thr Pro Tyr Ala Ile Ile Leu Asn Asn Gly Lys Glu Val Thr Arg
    340                 345                 350 caa aag atg agc tta acc gcc cgt cca gat gta gca gca gta tat cct      1334
Gln Lys Met Ser Leu Thr Ala Arg Pro Asp Val Ala Ala Val Tyr Pro
355                 360                 365                 370 tca ctt tat aat agt gct gtt agt ggt ttt gac act act att aaa ttg      1382
Ser Leu Tyr Asn Ser Ala Val Ser Gly Phe Asp Thr Thr Ile Lys Leu
                375                 380                 385 act aat gat caa tat caa gcg ctt aat ggc caa tta caa gta ttg tta      1430
Thr Asn Asp Gln Tyr Gln Ala Leu Asn Gly Gln Leu Gln Val Leu Leu
            390                 395                 400 cgt ttt tct aaa gct gct gat ggt aat cca agt ggt gat aat act gta      1478
Arg Phe Ser Lys Ala Ala Asp Gly Asn Pro Ser Gly Asp Asn Thr Val
        405                 410                 415 act gat caa ttt agt aaa aat tat gca act act ggt gga aac ttt gac      1526
Thr Asp Gln Phe Ser Lys Asn Tyr Ala Thr Thr Gly Gly Asn Phe Asp
    420                 425                 430 tat gta aaa gta aat ggt aat caa gtt gaa ttt agt ggt tgg cac gca      1574
Tyr Val Lys Val Asn Gly Asn Gln Val Glu Phe Ser Gly Trp His Ala
435                 440                 445                 450 act aac caa tca aat gat aaa gat tca caa tgg att att gtt tta gtt     1622
Thr Asn Gln Ser Asn Asp Lys Asp Ser Gln Trp Ile Ile Val Leu Val
                455                 460                 465 aat ggt aag gaa gta aag cgt caa tta gtt aat gat act aaa gag gga     1670
Asn Gly Lys Glu Val Lys Arg Gln Leu Val Asn Asp Thr Lys Glu Gly
            470                 475                 480 gct gct ggc ttc aac cga aac gat gtc tac aaa gta aat cca gct att     1718
Ala Ala Gly Phe Asn Arg Asn Asp Val Tyr Lys Val Asn Pro Ala Ile
        485                 490                 495 gaa aac agt tct atg tct gga ttc caa ggc att att act tta cct gtg     1766
Glu Asn Ser Ser Met Ser Gly Phe Gln Gly Ile Ile Thr Leu Pro Val
    500                 505                 510 aca gtt aaa aac gaa aat gtc caa ctt gtt cat cgg ttt agt aac gat     1814
Thr Val Lys Asn Glu Asn Val Gln Leu Val His Arg Phe Ser Asn Asp
515                 520                 525                 530 gtg aag act ggt gaa ggt aac tat gtt gat ttc tgg tca gag cta atg     1862
Val Lys Thr Gly Glu Gly Asn Tyr Val Asp Phe Trp Ser Glu Leu Met
                535                 540                 545 cct gtt aag gat agc ttc caa aag ggg aat ggc cca ctt aag caa ttt     1910
Pro Val Lys Asp Ser Phe Gln Lys Gly Asn Gly Pro Leu Lys Gln Phe
            550                 555                 560
```

```
ggc tta caa act att aac ggt caa caa tat tat att gac cca aca act    1958
Gly Leu Gln Thr Ile Asn Gly Gln Gln Tyr Tyr Ile Asp Pro Thr Thr
            565                 570                 575 ggt caa cca cgt aag aat ttc tta tta caa agt gga aat aat tgg att    2006
Gly Gln Pro Arg Lys Asn Phe Leu Leu Gln Ser Gly Asn Asn Trp Ile
        580                 585                 590 tac ttt gat agt gat act ggt gtg ggt act aat gca ctt gaa tta caa    2054
Tyr Phe Asp Ser Asp Thr Gly Val Gly Thr Asn Ala Leu Glu Leu Gln
595                 600                 605                 610 ttt gca aag gga act gtt tca tct aat gaa caa tac cgt aac ggt aat    2102
Phe Ala Lys Gly Thr Val Ser Ser Asn Glu Gln Tyr Arg Asn Gly Asn
                615                 620                 625 gca gct tac agt tat gat gac aag agt atc gaa aat gta aat ggt tac    2150
Ala Ala Tyr Ser Tyr Asp Asp Lys Ser Ile Glu Asn Val Asn Gly Tyr
            630                 635                 640 tta aca gca gat aca tgg tac cgt cca aaa cag atc tta aag gat gga    2198
Leu Thr Ala Asp Thr Trp Tyr Arg Pro Lys Gln Ile Leu Lys Asp Gly
        645                 650                 655 act acc tgg act gac tca aaa gaa aca gat atg cga cca atc ttg atg    2246
Thr Thr Trp Thr Asp Ser Lys Glu Thr Asp Met Arg Pro Ile Leu Met
    660                 665                 670 gta tgg tgg cct aat act ctt acc caa gca tac tac ctt aat tac atg    2294
Val Trp Trp Pro Asn Thr Leu Thr Gln Ala Tyr Tyr Leu Asn Tyr Met
675                 680                 685                 690 aaa caa cat ggt aat tta tta cca tct gct tta cca ttc ttt aat gcg    2342
Lys Gln His Gly Asn Leu Leu Pro Ser Ala Leu Pro Phe Phe Asn Ala
                695                 700                 705 gat gct gat cct gca gaa tta aat cat tat tcc gaa att gtg caa caa    2390
Asp Ala Asp Pro Ala Glu Leu Asn His Tyr Ser Glu Ile Val Gln Gln
            710                 715                 720 aat att gaa aaa cga att agt gaa acc gga aat act gat tgg tta cgt    2438
Asn Ile Glu Lys Arg Ile Ser Glu Thr Gly Asn Thr Asp Trp Leu Arg
        725                 730                 735 act tta atg cac gat ttt gtt act aac aat ccg atg tgg aat aag gat    2486
Thr Leu Met His Asp Phe Val Thr Asn Asn Pro Met Trp Asn Lys Asp
    740                 745                 750 agt gaa aat gtt aac ttt agt ggt att caa ttc caa ggc gga ttc tta    2534
Ser Glu Asn Val Asn Phe Ser Gly Ile Gln Phe Gln Gly Gly Phe Leu
755                 760                 765                 770 aag tat gaa aac tca gat tta acg cct tat gct aac tct gat tat cgc    2582
Lys Tyr Glu Asn Ser Asp Leu Thr Pro Tyr Ala Asn Ser Asp Tyr Arg
                775                 780                 785 tta ctt ggt cgg atg cca atc aat att aag gat caa aca tat cgg gga    2630
Leu Leu Gly Arg Met Pro Ile Asn Ile Lys Asp Gln Thr Tyr Arg Gly
            790                 795                 800 caa gaa ttc cta ctt gct aac gat att gat aac tct aat cct gtt gtt    2678
Gln Glu Phe Leu Leu Ala Asn Asp Ile Asp Asn Ser Asn Pro Val Val
        805                 810                 815 caa gca gaa caa tta aac tgg tta tac tat ctc ttg aac ttt gga acg    2726
Gln Ala Glu Gln Leu Asn Trp Leu Tyr Tyr Leu Leu Asn Phe Gly Thr
    820                 825                 830 atc aca gct aat aat gat caa gct aat ttt gat tct gta cgg gta gat    2774
Ile Thr Ala Asn Asn Asp Gln Ala Asn Phe Asp Ser Val Arg Val Asp
835                 840                 845                 850 gca ccg gat aat att gat gcc gat ctt atg aat atc gct cag gac tac    2822
Ala Pro Asp Asn Ile Asp Ala Asp Leu Met Asn Ile Ala Gln Asp Tyr
                855                 860                 865 ttt aat gct gca tat ggt atg gac tca gat gct gtc tca aat aag cat    2870
Phe Asn Ala Ala Tyr Gly Met Asp Ser Asp Ala Val Ser Asn Lys His
```

```
                    870                     875                     880
att aat att ctt gaa gac tgg aat cat gct gat ccg gaa tac ttt aat    2918
Ile Asn Ile Leu Glu Asp Trp Asn His Ala Asp Pro Glu Tyr Phe Asn
                885                     890                     895 aag atc gga aat cca caa ttg aca atg gat gat act att aag aat tcc    2966
Lys Ile Gly Asn Pro Gln Leu Thr Met Asp Asp Thr Ile Lys Asn Ser
900                     905                     910 ctg aat cat ggg ctt tca gat gca act aat cgt tgg gga tta gat gca    3014
Leu Asn His Gly Leu Ser Asp Ala Thr Asn Arg Trp Gly Leu Asp Ala
915                     920                     925                     930 att gtt cat cag tca tta gct gat cgt gaa aat aat tcc acg gaa aat    3062
Ile Val His Gln Ser Leu Ala Asp Arg Glu Asn Asn Ser Thr Glu Asn
                935                     940                     945 gtt gta att cct aat tac agt ttc gtt cgg gct cac gat aat aat tct    3110
Val Val Ile Pro Asn Tyr Ser Phe Val Arg Ala His Asp Asn Asn Ser
                950                     955                     960 caa gat caa att caa aat gct att cgt gat gta aca ggc aaa gat tac    3158
Gln Asp Gln Ile Gln Asn Ala Ile Arg Asp Val Thr Gly Lys Asp Tyr
                965                     970                     975 cat act ttc act ttt gaa gat gag caa aag ggt att gat gcg tac att    3206
His Thr Phe Thr Phe Glu Asp Glu Gln Lys Gly Ile Asp Ala Tyr Ile
980                     985                     990 caa gat caa aat tca aca gtg aag aaa tat aac ctt tat aat att ccg    3254
Gln Asp Gln Asn Ser Thr Val Lys Lys Tyr Asn Leu Tyr Asn Ile Pro
995                     1000                    1005                    1010 gct tca tac gca att ctt tta act aac aag gat aca att cca cgt gta    3302
Ala Ser Tyr Ala Ile Leu Leu Thr Asn Lys Asp Thr Ile Pro Arg Val
                1015                    1020                    1025 tac tat ggt gac ttg tat act gat ggt ggc caa tac atg gaa cat caa    3350
Tyr Tyr Gly Asp Leu Tyr Thr Asp Gly Gly Gln Tyr Met Glu His Gln
                1030                    1035                    1040 aca cgt tac tat gat act tta acg aac ctg ctt aaa tca cga gtt aag    3398
Thr Arg Tyr Tyr Asp Thr Leu Thr Asn Leu Leu Lys Ser Arg Val Lys
                1045                    1050                    1055 tat gtt gcc ggt ggc caa tca atg caa aca atg agc gtt ggc ggc aat    3446
Tyr Val Ala Gly Gly Gln Ser Met Gln Thr Met Ser Val Gly Gly Asn
                1060                    1065                    1070 aat aac att tta act agt gtt cgt tat ggt aaa ggt gcg atg aca gct    3494
Asn Asn Ile Leu Thr Ser Val Arg Tyr Gly Lys Gly Ala Met Thr Ala
1075                    1080                    1085                    1090 act gat act ggt act gat gaa acc aga aca caa ggt att ggg gtt gtt    3542
Thr Asp Thr Gly Thr Asp Glu Thr Arg Thr Gln Gly Ile Gly Val Val
                1095                    1100                    1105 gta agt aat acg cca aat cta aag cta ggt gtc aac gat aaa gta gtt    3590
Val Ser Asn Thr Pro Asn Leu Lys Leu Gly Val Asn Asp Lys Val Val
                1110                    1115                    1120 ctt cat atg gga gct gcg cac aag aac caa caa tat cgg gca gcc gtg    3638
Leu His Met Gly Ala Ala His Lys Asn Gln Gln Tyr Arg Ala Ala Val
                1125                    1130                    1135 ttg acg aca act gat gga gtc att aat tat act tct gat caa ggg gca    3686
Leu Thr Thr Thr Asp Gly Val Ile Asn Tyr Thr Ser Asp Gln Gly Ala
                1140                    1145                    1150 ccg gtt gca atg act gac gag aac ggt gat cta tac tta tct agt cat    3734
Pro Val Ala Met Thr Asp Glu Asn Gly Asp Leu Tyr Leu Ser Ser His
1155                    1160                    1165                    1170 aac cta gtt gtt aat ggt aaa gaa gaa gca gat aca gct gtt caa ggt    3782
Asn Leu Val Val Asn Gly Lys Glu Glu Ala Asp Thr Ala Val Gln Gly
                1175                    1180                    1185 tat gct aac cct gat gtt tca gga tat ctt gct gta tgg gta cca gtt    3830
```

```
                                                          -continued

Tyr Ala Asn Pro Asp Val Ser Gly Tyr Leu Ala Val Trp Val Pro Val
        1190                1195                1200 gga gca agt gat aac caa gat gct cga act gct cca tct act gaa aag       3878
Gly Ala Ser Asp Asn Gln Asp Ala Arg Thr Ala Pro Ser Thr Glu Lys
    1205                1210                1215 aat agt ggt aac tct gca tac aga aca aat gct gct ttt gat tca aat       3926
Asn Ser Gly Asn Ser Ala Tyr Arg Thr Asn Ala Ala Phe Asp Ser Asn
1220                1225                1230 gtt att ttt gaa gcc ttt tct aac ttt gtc tat aca cca aca aag gaa       3974
Val Ile Phe Glu Ala Phe Ser Asn Phe Val Tyr Thr Pro Thr Lys Glu
1235                1240                1245                1250 agt gaa cgt gct aat gtt cga att gcc caa aat gct gat ttc ttt gct       4022
Ser Glu Arg Ala Asn Val Arg Ile Ala Gln Asn Ala Asp Phe Phe Ala
        1255                1260                1265 tca tta ggt ttt act tct ttc gag atg gcg cca caa tat aat tca agt       4070
Ser Leu Gly Phe Thr Ser Phe Glu Met Ala Pro Gln Tyr Asn Ser Ser
    1270                1275                1280 aaa gat cgc aca ttc cta gat tca aca att gat aac gga tat gcg ttt       4118
Lys Asp Arg Thr Phe Leu Asp Ser Thr Ile Asp Asn Gly Tyr Ala Phe
1285                1290                1295 act gat cgt tat gat ctt gga atg agt gag cct aat aag tac gga aca       4166
Thr Asp Arg Tyr Asp Leu Gly Met Ser Glu Pro Asn Lys Tyr Gly Thr
    1300                1305                1310 gat gaa gat cta cgt aat gcc att caa gcg ctc cat aaa gct ggc tta       4214
Asp Glu Asp Leu Arg Asn Ala Ile Gln Ala Leu His Lys Ala Gly Leu
1315                1320                1325                1330 caa gta atg gcg gat tgg gtt cct gac caa atc tat aac ctt cct gga       4262
Gln Val Met Ala Asp Trp Val Pro Asp Gln Ile Tyr Asn Leu Pro Gly
        1335                1340                1345 aaa gaa gtt gct aca gtc act cga gta gat gat cgt ggt aat gta tgg       4310
Lys Glu Val Ala Thr Val Thr Arg Val Asp Asp Arg Gly Asn Val Trp
    1350                1355                1360 aaa gat gct atc att aat aat aat ctg tat gtt gtt aat act att ggt       4358
Lys Asp Ala Ile Ile Asn Asn Asn Leu Tyr Val Val Asn Thr Ile Gly
1365                1370                1375 ggt ggc gaa tac cag aag aag tat ggt gga gca ttc ctc gat aag tta       4406
Gly Gly Glu Tyr Gln Lys Lys Tyr Gly Gly Ala Phe Leu Asp Lys Leu
    1380                1385                1390 caa aaa ctt tat cct gaa atc ttc aca aag aag caa gtt tca act ggt       4454
Gln Lys Leu Tyr Pro Glu Ile Phe Thr Lys Lys Gln Val Ser Thr Gly
1395                1400                1405                1410 gtt gct att gat cct tca caa aag ata act gaa tgg tca gca aaa tac       4502
Val Ala Ile Asp Pro Ser Gln Lys Ile Thr Glu Trp Ser Ala Lys Tyr
        1415                1420                1425 ttt aat gga aca aac att ctc cat cgt ggt tct ggt tat gta cta aaa       4550
Phe Asn Gly Thr Asn Ile Leu His Arg Gly Ser Gly Tyr Val Leu Lys
    1430                1435                1440 gct gat ggt ggt caa tac tac aac tta ggt act act aca aag caa ttc       4598
Ala Asp Gly Gly Gln Tyr Tyr Asn Leu Gly Thr Thr Thr Lys Gln Phe
1445                1450                1455 ttg cca att caa tta act ggt gaa aag aaa caa gga aat gaa ggc ttt       4646
Leu Pro Ile Gln Leu Thr Gly Glu Lys Lys Gln Gly Asn Glu Gly Phe
    1460                1465                1470 gtt aag ggt aat gat gga aat tac tac ttc tat gac tta gca ggt aat       4694
Val Lys Gly Asn Asp Gly Asn Tyr Tyr Phe Tyr Asp Leu Ala Gly Asn
1475                1480                1485                1490 atg gtt aag aat acc ttt att gaa gat agt gtt ggc aac tgg tac ttc       4742
Met Val Lys Asn Thr Phe Ile Glu Asp Ser Val Gly Asn Trp Tyr Phe
        1495                1500                1505
```

```
ttt gac caa gat ggt aag atg gtt gaa aat aaa cat ttc gtt gat gtt       4790
Phe Asp Gln Asp Gly Lys Met Val Glu Asn Lys His Phe Val Asp Val
        1510                1515                1520 gat tct tat ggt gaa aaa ggt act tac ttc ttc ttg aag aat ggt gta       4838
Asp Ser Tyr Gly Glu Lys Gly Thr Tyr Phe Phe Leu Lys Asn Gly Val
    1525                1530                1535 tca ttc cgt ggg gga tta gtg caa act gac aat ggt act tat tac ttt       4886
Ser Phe Arg Gly Gly Leu Val Gln Thr Asp Asn Gly Thr Tyr Tyr Phe
1540                1545                1550 gat aat tat gga aag atg gta cgt aat caa act att aat gca ggt gcc       4934
Asp Asn Tyr Gly Lys Met Val Arg Asn Gln Thr Ile Asn Ala Gly Ala
1555                1560                1565                1570 atg att tat acc tta gat gaa aac ggt aag ctt ata aag gct agt tat       4982
Met Ile Tyr Thr Leu Asp Glu Asn Gly Lys Leu Ile Lys Ala Ser Tyr
            1575                1580                1585 aat tca gat gcc gaa tat cca act tca act gat gtt ggt aag atg ctt       5030
Asn Ser Asp Ala Glu Tyr Pro Thr Ser Thr Asp Val Gly Lys Met Leu
        1590                1595                1600 gat caa aat aaa cta taattagctg atttccgttt cttagaatcg aaagatttaa       5085
Asp Gln Asn Lys Leu
        1605 taactggggt taaaacggcc ctacaaaatc tgatattgat atagagatat tatttcctat    5145 atcaatatca gattttgct  ttttataaaa ttgattgtga ctaataagaa tccggaagat    5205 aacgttgttg ttatatcagt ggatttaagc aacatgaatt aattgaagat gacggcaatg    5265 attaaaagtc ggtctgatga tattgatgt attactagta tttggttttt atcatttata    5325 tttttactgt tattggtgtc atatattcca cataacagt aaaggtatat atgctagttt    5385 atttttaag taattataat attctgatta taatttggaa atattcgctt ttagcaaaaa    5445 ggtagtaaac agatcagaat cgtcattctg cttttctact actaaaagtc tgttttaaat    5505 tctaaactaa aataggctaa acactgatgt ttatcattta tatttttact gtt           5558

<210> SEQ ID NO 2
<211> LENGTH: 329
<212> TYPE: PRT
<213> ORGANISM: Lactobacillus reuteri

<400> SEQUENCE: 2

Ser Thr Ser Thr Pro Val Ser Val Leu Pro Ser Asn Thr Glu Lys
  1               5                  10                  15

Gln Ala Lys Asn Tyr Asn Glu Gln Asp Lys Gly Asn Tyr Gly Asn Ile
            20                  25                  30

Asp Thr Ala Tyr Phe Ser Asn Asn Gln Leu His Val Ser Gly Trp Asn
        35                  40                  45

Ala Thr Asn Ala Ser Gln Gly Thr Asn Ser Arg Gln Ile Ile Val Arg
    50                  55                  60

Asp Ile Thr Thr Asn Glu Leu Gly Arg Thr Asp Val Thr Asn Asn
65                  70                  75                  80

Val Ala Arg Pro Asp Val Lys Asn Val His Asn Val Tyr Asn Ala Asp
                85                  90                  95

Asn Ser Gly Phe Asp Val Asn Val Asn Ile Asp Phe Ser Lys Met Lys
            100                 105                 110

Asp Tyr Arg Asp Ser Ile Glu Ile Val Ser Arg Tyr Ser Gly Asn Gly
        115                 120                 125

Lys Ser Val Asp Trp Trp Ser Gln Pro Ile Thr Phe Asp Lys Asn Asn
    130                 135                 140
```

```
Tyr Ala Tyr Leu Asp Thr Phe Glu Val Lys Asn Gly Glu Leu His Ala
145                 150                 155                 160

Thr Gly Trp Asn Ala Thr Asn Ser Ala Ile Asn Tyr Asn His His Phe
            165                 170                 175

Val Ile Leu Phe Asp Gln Thr Asn Gly Lys Glu Val Ala Arg Gln Glu
            180                 185                 190

Val Arg Glu Gly Gln Ser Arg Pro Asp Val Ala Lys Val Tyr Pro Gln
        195                 200                 205

Val Val Gly Ala Ala Asn Ser Gly Phe Asn Val Thr Phe Asn Ile Ser
210                 215                 220

Asp Leu Asp Tyr Thr His Gln Tyr Gln Val Leu Ser Arg Tyr Ser Asn
225                 230                 235                 240

Ser Asp Asn Gly Glu Gly Asp Asn Val Thr Tyr Trp Phe Asn Pro Gln
            245                 250                 255

Ser Ile Ala Pro Ala Asn Gln Ser Asn Gln Gly Tyr Leu Asp Ser Phe
            260                 265                 270

Asp Ile Ser Lys Asn Gly Glu Val Thr Val Thr Gly Trp Asn Ala Thr
        275                 280                 285

Asp Leu Ser Glu Leu Gln Asn Asn His Tyr Val Ile Leu Phe Asp Gln
290                 295                 300

Thr Ala Gly Lys Gln Val Ala Ser Ala Lys Ala Asp Leu Ile Ser Arg
305                 310                 315                 320

Pro Asp Val Ala Lys Ala Tyr Pro Gln
                325
```

<210> SEQ ID NO 3
<211> LENGTH: 1278
<212> TYPE: PRT
<213> ORGANISM: Lactobacillus reuteri

<400> SEQUENCE: 3

```
Met Ala Ser Asp Asn Ser Ile Asn Glu Thr Thr Pro Tyr Ala Ile Ile
1               5                   10                  15

Leu Asn Asn Gly Lys Glu Val Thr Arg Gln Lys Met Ser Leu Thr Ala
            20                  25                  30

Arg Pro Asp Val Ala Val Tyr Pro Ser Leu Tyr Asn Ser Ala Val
        35                  40                  45

Ser Gly Phe Asp Thr Thr Ile Lys Leu Thr Asn Asp Gln Tyr Gln Ala
    50                  55                  60

Leu Asn Gly Gln Leu Gln Val Leu Leu Arg Phe Ser Lys Ala Ala Asp
65                  70                  75                  80

Gly Asn Pro Ser Gly Asp Asn Thr Val Thr Asp Gln Phe Ser Lys Asn
            85                  90                  95

Tyr Ala Thr Thr Gly Gly Asn Phe Asp Tyr Val Lys Val Asn Gly Asn
            100                 105                 110

Gln Val Glu Phe Ser Gly Trp His Ala Thr Asn Gln Ser Asn Asp Lys
        115                 120                 125

Asp Ser Gln Trp Ile Ile Val Leu Val Asn Gly Lys Glu Val Lys Arg
130                 135                 140

Gln Leu Val Asn Asp Thr Lys Glu Gly Ala Ala Gly Phe Asn Arg Asn
145                 150                 155                 160

Asp Val Tyr Lys Val Asn Pro Ala Ile Glu Asn Ser Ser Met Ser Gly
            165                 170                 175

Phe Gln Gly Ile Ile Thr Leu Pro Val Thr Val Lys Asn Glu Asn Val
        180                 185                 190
```

-continued

```
Gln Leu Val His Arg Phe Ser Asn Asp Val Lys Thr Gly Glu Gly Asn
            195                 200                 205

Tyr Val Asp Phe Trp Ser Glu Leu Met Pro Val Lys Asp Ser Phe Gln
210                 215                 220

Lys Gly Asn Gly Pro Leu Lys Gln Phe Gly Leu Gln Thr Ile Asn Gly
225                 230                 235                 240

Gln Gln Tyr Tyr Ile Asp Pro Thr Thr Gly Gln Pro Arg Lys Asn Phe
                245                 250                 255

Leu Leu Gln Ser Gly Asn Asn Trp Ile Tyr Phe Asp Ser Asp Thr Gly
            260                 265                 270

Val Gly Thr Asn Ala Leu Glu Leu Gln Phe Ala Lys Gly Thr Val Ser
            275                 280                 285

Ser Asn Glu Gln Tyr Arg Asn Gly Asn Ala Ala Tyr Ser Tyr Asp Asp
290                 295                 300

Lys Ser Ile Glu Asn Val Asn Gly Tyr Leu Thr Ala Asp Thr Trp Tyr
305                 310                 315                 320

Arg Pro Lys Gln Ile Leu Lys Asp Gly Thr Thr Trp Thr Asp Ser Lys
                325                 330                 335

Glu Thr Asp Met Arg Pro Ile Leu Met Val Trp Trp Pro Asn Thr Leu
            340                 345                 350

Thr Gln Ala Tyr Tyr Leu Asn Tyr Met Lys Gln His Gly Asn Leu Leu
            355                 360                 365

Pro Ser Ala Leu Pro Phe Phe Asn Ala Asp Ala Asp Pro Ala Glu Leu
            370                 375                 380

Asn His Tyr Ser Glu Ile Val Gln Gln Asn Ile Glu Lys Arg Ile Ser
385                 390                 395                 400

Glu Thr Gly Asn Thr Asp Trp Leu Arg Thr Leu Met His Asp Phe Val
                405                 410                 415

Thr Asn Asn Pro Met Trp Asn Lys Asp Ser Glu Asn Val Asn Phe Ser
            420                 425                 430

Gly Ile Gln Phe Gln Gly Gly Phe Leu Lys Tyr Glu Asn Ser Asp Leu
            435                 440                 445

Thr Pro Tyr Ala Asn Ser Asp Tyr Arg Leu Leu Gly Arg Met Pro Ile
450                 455                 460

Asn Ile Lys Asp Gln Thr Tyr Arg Gly Gln Glu Phe Leu Leu Ala Asn
465                 470                 475                 480

Asp Ile Asp Asn Ser Asn Pro Val Val Gln Ala Glu Gln Leu Asn Trp
                485                 490                 495

Leu Tyr Tyr Leu Leu Asn Phe Gly Thr Ile Thr Ala Asn Asn Asp Gln
            500                 505                 510

Ala Asn Phe Asp Ser Val Arg Val Asp Ala Pro Asp Asn Ile Asp Ala
            515                 520                 525

Asp Leu Met Asn Ile Ala Gln Asp Tyr Phe Asn Ala Ala Tyr Gly Met
            530                 535                 540

Asp Ser Asp Ala Val Ser Asn Lys His Ile Asn Ile Leu Glu Asp Trp
545                 550                 555                 560

Asn His Ala Asp Pro Glu Tyr Phe Asn Lys Ile Gly Asn Pro Gln Leu
                565                 570                 575

Thr Met Asp Asp Thr Ile Lys Asn Ser Leu Asn His Gly Leu Ser Asp
            580                 585                 590

Ala Thr Asn Arg Trp Gly Leu Asp Ala Ile Val His Gln Ser Leu Ala
            595                 600                 605
```

```
Asp Arg Glu Asn Asn Ser Thr Glu Asn Val Val Ile Pro Asn Tyr Ser
    610                 615                 620

Phe Val Arg Ala His Asp Asn Ser Gln Asp Gln Ile Gln Asn Ala
625                 630                 635                 640

Ile Arg Asp Val Thr Gly Lys Asp Tyr His Thr Phe Thr Phe Glu Asp
                    645                 650                 655

Glu Gln Lys Gly Ile Asp Ala Tyr Ile Gln Asp Gln Asn Ser Thr Val
                660                 665                 670

Lys Lys Tyr Asn Leu Tyr Asn Ile Pro Ala Ser Tyr Ala Ile Leu Leu
            675                 680                 685

Thr Asn Lys Asp Thr Ile Pro Arg Val Tyr Tyr Gly Asp Leu Tyr Thr
        690                 695                 700

Asp Gly Gly Gln Tyr Met Glu His Gln Thr Arg Tyr Tyr Asp Thr Leu
705                 710                 715                 720

Thr Asn Leu Leu Lys Ser Arg Val Lys Tyr Val Ala Gly Gly Gln Ser
                    725                 730                 735

Met Gln Thr Met Ser Val Gly Gly Asn Asn Asn Ile Leu Thr Ser Val
                740                 745                 750

Arg Tyr Gly Lys Gly Ala Met Thr Ala Thr Asp Thr Gly Thr Asp Glu
            755                 760                 765

Thr Arg Thr Gln Gly Ile Gly Val Val Ser Asn Thr Pro Asn Leu
        770                 775                 780

Lys Leu Gly Val Asn Asp Lys Val Val Leu His Met Gly Ala Ala His
785                 790                 795                 800

Lys Asn Gln Gln Tyr Arg Ala Ala Val Leu Thr Thr Thr Asp Gly Val
                    805                 810                 815

Ile Asn Tyr Thr Ser Asp Gln Gly Ala Pro Val Ala Met Thr Asp Glu
                820                 825                 830

Asn Gly Asp Leu Tyr Leu Ser Ser His Asn Leu Val Val Asn Gly Lys
            835                 840                 845

Glu Glu Ala Asp Thr Ala Val Gln Gly Tyr Ala Asn Pro Asp Val Ser
        850                 855                 860

Gly Tyr Leu Ala Val Trp Val Pro Val Gly Ala Ser Asp Asn Gln Asp
865                 870                 875                 880

Ala Arg Thr Ala Pro Ser Thr Glu Lys Asn Ser Gly Asn Ser Ala Tyr
                    885                 890                 895

Arg Thr Asn Ala Ala Phe Asp Ser Asn Val Ile Phe Glu Ala Phe Ser
                900                 905                 910

Asn Phe Val Tyr Thr Pro Thr Lys Glu Ser Glu Arg Ala Asn Val Arg
            915                 920                 925

Ile Ala Gln Asn Ala Asp Phe Phe Ala Ser Leu Gly Phe Thr Ser Phe
        930                 935                 940

Glu Met Ala Pro Gln Tyr Asn Ser Ser Lys Asp Arg Thr Phe Leu Asp
945                 950                 955                 960

Ser Thr Ile Asp Asn Gly Tyr Ala Phe Thr Asp Arg Tyr Asp Leu Gly
                    965                 970                 975

Met Ser Glu Pro Asn Lys Tyr Gly Thr Asp Glu Asp Leu Arg Asn Ala
                980                 985                 990

Ile Gln Ala Leu His Lys Ala Gly Leu Gln Val Met Ala Asp Trp Val
            995                 1000                1005

Pro Asp Gln Ile Tyr Asn Leu Pro Gly Lys Glu Val Ala Thr Val Thr
        1010                1015                1020

Arg Val Asp Asp Arg Gly Asn Val Trp Lys Asp Ala Ile Ile Asn Asn
```

```
                    1025                1030                1035                1040
Asn Leu Tyr Val Val Asn Thr Ile Gly Gly Gly Glu Tyr Gln Lys Lys
                1045                1050                1055

Tyr Gly Gly Ala Phe Leu Asp Lys Leu Gln Lys Leu Tyr Pro Glu Ile
            1060                1065                1070

Phe Thr Lys Lys Gln Val Ser Thr Gly Val Ala Ile Asp Pro Ser Gln
        1075                1080                1085

Lys Ile Thr Glu Trp Ser Ala Lys Tyr Phe Asn Gly Thr Asn Ile Leu
    1090                1095                1100

His Arg Gly Ser Gly Tyr Val Leu Lys Ala Asp Gly Gly Gln Tyr Tyr
1105                1110                1115                1120

Asn Leu Gly Thr Thr Thr Lys Gln Phe Leu Pro Ile Gln Leu Thr Gly
                1125                1130                1135

Glu Lys Lys Gln Gly Asn Glu Gly Phe Val Lys Gly Asn Asp Gly Asn
            1140                1145                1150

Tyr Tyr Phe Tyr Asp Leu Ala Gly Asn Met Val Lys Asn Thr Phe Ile
        1155                1160                1165

Glu Asp Ser Val Gly Asn Trp Tyr Phe Asp Gln Asp Gly Lys Met
    1170                1175                1180

Val Glu Asn Lys His Phe Val Asp Val Asp Ser Tyr Gly Glu Lys Gly
1185                1190                1195                1200

Thr Tyr Phe Phe Leu Lys Asn Gly Val Ser Phe Arg Gly Gly Leu Val
                1205                1210                1215

Gln Thr Asp Asn Gly Thr Tyr Tyr Phe Asp Asn Tyr Gly Lys Met Val
            1220                1225                1230

Arg Asn Gln Thr Ile Asn Ala Gly Ala Met Ile Tyr Thr Leu Asp Glu
        1235                1240                1245

Asn Gly Lys Leu Ile Lys Ala Ser Tyr Asn Ser Asp Ala Glu Tyr Pro
    1250                1255                1260

Thr Ser Thr Asp Val Gly Lys Met Leu Asp Gln Asn Lys Leu
1265                1270                1275

<210> SEQ ID NO 4
<211> LENGTH: 545
<212> TYPE: PRT
<213> ORGANISM: Streptococcus mutans

<400> SEQUENCE: 4

Leu Leu Ala Asn Asp Ile Asp Asn Ser Asn Pro Val Val Gln Ala Glu
  1               5                  10                  15

Gln Leu Asn Trp Leu His Tyr Leu Met Asn Tyr Gly Ser Ile Val Ala
             20                  25                  30

Asn Asp Pro Glu Ala Asn Phe Asp Gly Val Arg Val Asp Ala Val Asp
         35                  40                  45

Asn Val Asn Ala Asp Leu Leu Gln Ile Ala Ser Asp Tyr Leu Lys Ala
     50                  55                  60

His Tyr Gly Val Asp Lys Ser Glu Lys Asn Ala Ile Asn His Leu Ser
 65                  70                  75                  80

Ile Leu Glu Ala Trp Ser Asp Asn Asp Pro Gln Tyr Asn Lys Asp Thr
                 85                  90                  95

Lys Gly Ala Gln Leu Pro Ile Asp Asn Lys Leu Arg Leu Ser Leu Leu
            100                 105                 110

Tyr Ala Leu Thr Arg Pro Leu Glu Lys Asp Ala Ser Asn Lys Asn Glu
        115                 120                 125
```

-continued

```
Ile Arg Ser Gly Leu Glu Pro Val Ile Thr Asn Ser Leu Asn Asn Arg
    130                 135                 140

Ser Ala Glu Gly Lys Asn Ser Glu Arg Met Ala Asn Tyr Ile Phe Ile
145                 150                 155                 160

Arg Ala His Asp Ser Glu Val Gln Thr Val Ile Ala Lys Ile Ile Lys
                    165                 170                 175

Ala Gln Ile Asn Pro Lys Thr Asp Gly Leu Thr Phe Thr Leu Asp Glu
                180                 185                 190

Leu Lys Gln Ala Phe Lys Ile Tyr Asn Glu Asp Met Arg Gln Ala Lys
            195                 200                 205

Lys Lys Tyr Thr Gln Ser Asn Ile Pro Thr Ala Tyr Ala Leu Met Leu
        210                 215                 220

Ser Asn Lys Asp Ser Ile Thr Arg Leu Tyr Tyr Gly Asp Met Tyr Ser
225                 230                 235                 240

Asp Asp Gly Gln Tyr Met Ala Thr Lys Ser Pro Tyr Tyr Asp Ala Ile
                    245                 250                 255

Asp Thr Leu Leu Lys Ala Arg Ile Lys Tyr Ala Ala Gly Gly Gln Asp
                260                 265                 270

Met Lys Ile Thr Tyr Val Glu Gly Asp Lys Ser His Met Asp Trp Asp
            275                 280                 285

Tyr Thr Gly Val Leu Thr Ser Val Arg Tyr Gly Thr Gly Ala Asn Glu
        290                 295                 300

Ala Thr Asp Gln Gly Ser Glu Ala Thr Lys Thr Gln Gly Met Ala Val
305                 310                 315                 320

Ile Thr Ser Asn Asn Pro Ser Leu Lys Leu Asn Gln Asn Asp Lys Val
                    325                 330                 335

Ile Val Asn Met Gly Ala Ala His Lys Asn Gln Glu Tyr Arg Pro Leu
                340                 345                 350

Leu Leu Thr Thr Lys Asp Gly Leu Thr Ser Tyr Thr Ser Asp Ala Ala
            355                 360                 365

Ala Lys Ser Leu Tyr Arg Lys Thr Asn Asp Lys Gly Glu Leu Val Phe
        370                 375                 380

Asp Ala Ser Asp Ile Gln Gly Tyr Leu Asn Pro Gln Val Ser Gly Tyr
385                 390                 395                 400

Leu Ala Val Trp Val Pro Val Gly Ala Ser Asp Asn Gln Asp Val Arg
                    405                 410                 415

Val Ala Ala Ser Asn Lys Ala Asn Ala Thr Gly Gln Val Tyr Glu Ser
                420                 425                 430

Ser Ser Ala Leu Asp Ser Gln Leu Ile Tyr Glu Gly Phe Ser Asn Phe
            435                 440                 445

Gln Asp Phe Val Thr Lys Asp Ser Asp Tyr Thr Asn Lys Lys Ile Ala
        450                 455                 460

Gln Asn Val Gln Leu Phe Lys Ser Trp Gly Val Thr Ser Phe Glu Met
465                 470                 475                 480

Ala Pro Gln Tyr Val Ser Ser Glu Asp Gly Ser Phe Leu Asp Ser Ile
                    485                 490                 495

Ile Gln Asn Gly Tyr Ala Phe Glu Asp Arg Tyr Asp Leu Ala Met Ser
                500                 505                 510

Lys Asn Asn Lys Tyr Gly Ser Gln Gln Asp Met Ile Asn Ala Val Lys
            515                 520                 525

Ala Leu His Lys Ser Gly Ile Gln Val Ile Ala Asp Trp Val Pro Asp
        530                 535                 540

Gln
```

545

<210> SEQ ID NO 5
<211> LENGTH: 523
<212> TYPE: PRT
<213> ORGANISM: Leuconostoc mesenteroides

<400> SEQUENCE: 5

```
Leu Leu Ala Asn Asp Val Asp Asn Ser Asn Val Val Glu Ala Glu
 1               5                  10                  15
Gln Leu Asn Trp Leu Tyr Tyr Leu Met Asn Phe Gly Thr Ile Thr Ala
                 20                  25                  30
Asn Asp Ala Asp Ala Asn Phe Asp Gly Ile Arg Val Asp Ala Val Asp
             35                  40                  45
Asn Val Asp Ala Asp Leu Leu Gln Ile Ala Ala Asp Tyr Lys Phe Leu
         50                  55                  60
Ala Tyr Gly Val Asp Gln Asn Asp Ala Thr Ala Asn Gln His Leu Ser
 65                  70                  75                  80
Ile Leu Glu Asp Trp Ser His Asn Asp Pro Leu Tyr Val Thr Asp Gln
                 85                  90                  95
Gly Ser Asn Gln Leu Thr Met Asp Asp Tyr Val His Thr Gln Leu Ile
            100                 105                 110
Trp Ser Leu Thr Lys Ser Ser Asp Ile Arg Gly Thr Met Gln Arg Phe
            115                 120                 125
Val Asp Tyr Tyr Met Val Asp Arg Ser Asn Asp Ser Thr Glu Asn Glu
            130                 135                 140
Ala Ile Pro Asn Tyr Ser Phe Val Arg Ala His Asp Ser Glu Val Gln
145                 150                 155                 160
Thr Val Ile Ala Gln Ile Val Ser Asp Leu Tyr Pro Asp Val Glu Asn
                165                 170                 175
Ser Leu Ala Pro Thr Thr Glu Gln Leu Ala Ala Phe Lys Val Tyr
                180                 185                 190
Asn Glu Asp Glu Lys Leu Ala Asp Lys Lys Tyr Thr Gln Tyr Asn Met
                195                 200                 205
Ala Ser Ala Tyr Ala Met Leu Leu Thr Asn Lys Asp Thr Val Pro Arg
210                 215                 220
Val Tyr Tyr Gly Asp Leu Tyr Thr Asp Asp Gly Gln Tyr Met Ala Thr
225                 230                 235                 240
Lys Ser Pro Tyr Tyr Asp Ala Ile Asn Thr Leu Leu Lys Ala Arg Val
                245                 250                 255
Gln Tyr Val Ala Gly Gly Gln Ser Met Ser Val Asp Ser Asn Asp Val
                260                 265                 270
Leu Thr Ser Val Arg Tyr Gly Lys Asp Ala Met Thr Ala Ser Asp Thr
            275                 280                 285
Gly Thr Ser Glu Thr Arg Thr Glu Gly Ile Gly Val Ile Val Ser Asn
            290                 295                 300
Asn Ala Glu Leu Gln Leu Glu Asp Gly His Thr Val Thr Leu His Met
305                 310                 315                 320
Gly Ala Ala His Lys Asn Gln Ala Tyr Arg Ala Leu Leu Ser Thr Thr
                325                 330                 335
Ala Asp Gly Leu Ala Tyr Tyr Asp Thr Asp Glu Asn Ala Pro Val Ala
            340                 345                 350
Tyr Thr Asp Ala Asn Gly Asp Leu Ile Phe Thr Asn Glu Ser Ile Tyr
            355                 360                 365
```

```
Gly Val Gln Asn Pro Gln Val Ser Gly Tyr Leu Ala Val Trp Val Pro
        370                 375                 380

Val Gly Ala Gln Gln Asp Gln Asp Ala Arg Thr Ala Ser Asp Thr Thr
385                 390                 395                 400

Thr Asn Thr Ser Asp Lys Val Phe His Ser Asn Ala Ala Leu Asp Ser
                405                 410                 415

Gln Val Ile Tyr Glu Gly Phe Ser Asn Phe Gln Ala Phe Ala Thr Asp
            420                 425                 430

Ser Ser Glu Tyr Thr Asn Val Val Ile Ala Gln Asn Ala Asp Gln Phe
                435                 440                 445

Lys Gln Trp Gly Val Thr Ser Phe Gln Leu Ala Pro Gln Tyr Arg Ser
        450                 455                 460

Ser Thr Asp Thr Ser Phe Leu Asp Ser Ile Ile Gln Asn Gly Tyr Ala
465                 470                 475                 480

Phe Thr Asp Arg Tyr Asp Leu Gly Tyr Gly Thr Pro Thr Lys Tyr Gly
                485                 490                 495

Thr Ala Asp Gln Leu Arg Asp Ala Ile Lys Ala Leu His Ala Ser Gly
            500                 505                 510

Ile Gln Ala Ile Ala Asp Trp Val Pro Asp Gln
        515                 520

<210> SEQ ID NO 6
<211> LENGTH: 584
<212> TYPE: PRT
<213> ORGANISM: Leuconostoc mesenteroides

<400> SEQUENCE: 6

Leu Leu Ala Asn Asp Ile Asp Asn Ser Asn Pro Ile Val Gln Ala Glu
1               5                   10                  15

Gln Leu Asn Trp Leu His Tyr Leu Met Asn Phe Gly Ser Ile Thr Gly
            20                  25                  30

Asn Asn Asp Asn Ala Asn Phe Asp Gly Ile Arg Val Asp Ala Val Asp
        35                  40                  45

Asn Val Asp Ala Asp Leu Leu Lys Ile Ala Gly Asp Tyr Phe Lys Ala
    50                  55                  60

Leu Tyr Gly Thr Asp Lys Ser Asp Ala Asn Ala Asn Lys His Leu Ser
65                  70                  75                  80

Ile Leu Glu Asp Trp Asn Gly Lys Asp Pro Gln Tyr Val Asn Gln Gln
                85                  90                  95

Gly Asn Ala Gln Leu Thr Met Asp Tyr Thr Val Thr Ser Gln Phe Gly
            100                 105                 110

Asn Ser Leu Thr His Gly Ala Asn Asn Arg Ser Asn Met Trp Tyr Phe
        115                 120                 125

Leu Asp Thr Gly Tyr Tyr Leu Asn Gly Asp Leu Asn Lys Lys Ile Val
    130                 135                 140

Asp Lys Asn Arg Pro Asn Ser Gly Thr Leu Val Asn Arg Ile Ala Asn
145                 150                 155                 160

Ser Gly Asp Thr Lys Val Ile Pro Asn Tyr Ser Phe Val Arg Ala His
                165                 170                 175

Asp Tyr Asp Ala Gln Asp Pro Ile Ser Lys Ala Met Ile Asp His Gly
            180                 185                 190

Ile Ile Lys Asn Met Gln Asp Thr Phe Thr Phe Asp Gln Leu Ala Gln
        195                 200                 205

Gly Met Glu Phe Tyr Tyr Lys Asp Gln Glu Asn Pro Ser Gly Phe Lys
    210                 215                 220
```

```
Lys Tyr Asn Asp Tyr Asn Leu Pro Ser Ala Tyr Ala Met Leu Leu Thr
225                 230                 235                 240

Asn Lys Asp Thr Val Pro Arg Val Tyr Tyr Gly Asp Met Tyr Leu Glu
            245                 250                 255

Gly Gly Gln Tyr Met Glu Lys Gly Thr Ile Tyr Asn Pro Val Ile Ser
        260                 265                 270

Ala Leu Leu Lys Ala Arg Ile Lys Tyr Val Ser Gly Gln Thr Met
        275                 280                 285

Ala Thr Asp Ser Ser Gly Lys Asp Leu Lys Asp Gly Thr Asp Leu
    290                 295                 300

Leu Thr Ser Val Arg Phe Gly Lys Gly Ile Met Thr Ser Asp Gln Thr
305                 310                 315                 320

Thr Thr Gln Asp Asn Ser Gln Asp Tyr Lys Asn Gln Gly Ile Gly Val
                325                 330                 335

Ile Val Gly Asn Asn Pro Asp Leu Lys Leu Asn Asn Asp Lys Thr Ile
                340                 345                 350

Thr Leu His Met Gly Lys Ala His Lys Asn Gln Leu Tyr Arg Ala Leu
                355                 360                 365

Val Leu Ser Asn Asp Ser Gly Ile Asp Val Tyr Asp Ser Asp Lys
370                 375                 380

Ala Pro Thr Leu Arg Thr Asn Asp Asn Gly Asp Leu Ile Phe His Lys
385                 390                 395                 400

Thr Asn Thr Phe Val Lys Gln Asp Gly Thr Ile Ile Asn Tyr Glu Met
                405                 410                 415

Lys Gly Ser Leu Asn Ala Leu Ile Ser Gly Tyr Leu Gly Val Trp Val
                420                 425                 430

Pro Val Gly Ala Ser Asp Ser Gln Asp Ala Arg Thr Val Ala Thr Glu
                435                 440                 445

Ser Ser Ser Asn Asp Gly Ser Val Phe His Ser Asn Ala Ala Leu
    450                 455                 460

Asp Ser Asn Val Ile Tyr Glu Gly Phe Ser Asn Phe Gln Ala Met Pro
465                 470                 475                 480

Thr Ser Pro Glu Gln Ser Thr Asn Val Val Ile Ala Thr Lys Ala Asn
                485                 490                 495

Leu Phe Lys Glu Leu Gly Ile Thr Ser Phe Glu Leu Ala Pro Gln Tyr
                500                 505                 510

Arg Ser Ser Gly Asp Thr Asn Tyr Gly Gly Met Ser Phe Leu Asp Ser
            515                 520                 525

Phe Leu Asn Asn Gly Tyr Ala Phe Thr Asp Arg Tyr Asp Leu Gly Phe
            530                 535                 540

Asn Lys Ala Asp Gly Asn Pro Asn Pro Thr Lys Tyr Gly Thr Asp Gln
545                 550                 555                 560

Asp Leu Arg Asn Ala Ile Glu Ala Leu His Lys Asn Gly Met Gln Ala
                565                 570                 575

Ile Ala Asp Trp Val Pro Asp Gln
            580
```

<210> SEQ ID NO 7
<211> LENGTH: 535
<212> TYPE: PRT
<213> ORGANISM: Lactobacillus reuteri

<400> SEQUENCE: 7

Leu Leu Ala Asn Asp Ile Asp Asn Ser Asn Pro Val Val Gln Ala Glu

```
            1                5                    10                    15
         Gln Leu Asn Trp Leu Tyr Tyr Leu Leu Asn Phe Gly Thr Ile Thr Ala
                         20                   25                    30
         Asn Asn Asp Gln Ala Asn Phe Asp Ser Val Arg Val Asp Ala Pro Asp
                     35                    40                    45
         Asn Ile Asp Ala Asp Leu Met Asn Ile Ala Gln Asp Tyr Phe Asn Ala
                 50                    55                    60
         Ala Tyr Gly Met Asp Ser Asp Ala Val Ser Asn Lys His Ile Asn Ile
         65                    70                    75                    80
         Leu Glu Asp Trp Asn His Ala Asp Pro Glu Tyr Phe Asn Lys Ile Gly
                             85                    90                    95
         Asn Pro Gln Leu Thr Met Asp Asp Thr Ile Lys Asn Ser Leu Asn His
                         100                   105                   110
         Gly Leu Ser Asp Ala Thr Asn Arg Trp Gly Leu Asp Ala Ile Val His
                     115                   120                   125
         Gln Ser Leu Ala Asp Arg Glu Asn Asn Ser Thr Glu Asn Val Val Ile
                 130                   135                   140
         Pro Asn Tyr Ser Phe Val Arg Ala His Asp Asn Asn Ser Gln Asp Gln
         145                   150                   155                   160
         Ile Gln Asn Ala Ile Arg Asp Val Thr Gly Lys Asp Tyr His Thr Phe
                             165                   170                   175
         Thr Phe Glu Asp Glu Gln Lys Gly Ile Asp Ala Tyr Ile Gln Asp Gln
                         180                   185                   190
         Asn Ser Thr Val Lys Lys Tyr Asn Leu Tyr Asn Ile Pro Ala Ser Tyr
                     195                   200                   205
         Ala Ile Leu Leu Thr Asn Lys Asp Thr Ile Pro Arg Val Tyr Tyr Gly
                 210                   215                   220
         Asp Leu Tyr Thr Asp Gly Gly Gln Tyr Met Glu His Gln Thr Arg Tyr
         225                   230                   235                   240
         Tyr Asp Thr Leu Thr Asn Leu Leu Lys Ser Arg Val Lys Tyr Val Ala
                             245                   250                   255
         Gly Gly Gln Ser Met Gln Thr Met Ser Val Gly Asn Asn Asn Ile
                         260                   265                   270
         Leu Thr Ser Val Arg Tyr Gly Lys Gly Ala Met Thr Ala Thr Asp Thr
                     275                   280                   285
         Gly Thr Asp Glu Thr Arg Thr Gln Gly Ile Gly Val Val Ser Asn
         290                   295                   300
         Thr Pro Asn Leu Lys Leu Gly Val Asn Asp Lys Val Val Leu His Met
         305                   310                   315                   320
         Gly Ala Ala His Lys Asn Gln Gln Tyr Arg Ala Ala Val Leu Thr Thr
                             325                   330                   335
         Thr Asp Gly Val Ile Asn Tyr Thr Ser Asp Gln Gly Ala Pro Val Ala
                         340                   345                   350
         Met Thr Asp Glu Asn Gly Asp Leu Tyr Leu Ser Ser His Asn Leu Val
                     355                   360                   365
         Val Asn Gly Lys Glu Glu Ala Asp Thr Ala Val Gln Gly Tyr Ala Asn
                 370                   375                   380
         Pro Asp Val Ser Gly Tyr Leu Ala Val Trp Val Pro Val Gly Ala Ser
         385                   390                   395                   400
         Asp Asn Gln Asp Ala Arg Thr Ala Pro Ser Thr Glu Lys Asn Ser Gly
                             405                   410                   415
         Asn Ser Ala Tyr Arg Thr Asn Ala Ala Phe Asp Ser Asn Val Ile Phe
                         420                   425                   430
```

```
Glu Ala Phe Ser Asn Phe Val Tyr Thr Pro Thr Lys Glu Ser Glu Arg
        435                 440                 445

Ala Asn Val Arg Ile Ala Gln Asn Ala Asp Phe Phe Ala Ser Leu Gly
    450                 455                 460

Phe Thr Ser Phe Glu Met Ala Pro Gln Tyr Asn Ser Ser Lys Asp Arg
465                 470                 475                 480

Thr Phe Leu Asp Ser Thr Ile Asp Asn Gly Tyr Ala Phe Thr Asp Arg
                485                 490                 495

Tyr Asp Leu Gly Met Ser Glu Pro Asn Lys Tyr Gly Thr Asp Glu Asp
            500                 505                 510

Leu Arg Asn Ala Ile Gln Ala Leu His Lys Ala Gly Leu Gln Val Met
        515                 520                 525

Ala Asp Trp Val Pro Asp Gln
        530                 535

<210> SEQ ID NO 8
<211> LENGTH: 5
<212> TYPE: PRT
<213> ORGANISM: Neisseria polysaccharea

<400> SEQUENCE: 8

Gln Trp Asp Leu Asn
  1               5

<210> SEQ ID NO 9
<211> LENGTH: 10
<212> TYPE: PRT
<213> ORGANISM: Neisseria polysaccharea

<400> SEQUENCE: 9

Ile Val Arg Met Asp Ala Val Ala Phe Ile
  1               5                  10

<210> SEQ ID NO 10
<211> LENGTH: 6
<212> TYPE: PRT
<213> ORGANISM: Neisseria polysaccharea

<400> SEQUENCE: 10

Phe Val Arg Ser His Asp
  1               5

<210> SEQ ID NO 11
<211> LENGTH: 9
<212> TYPE: PRT
<213> ORGANISM: Neisseria polysaccharea

<400> SEQUENCE: 11

Gly Leu Pro Arg Ile Tyr Leu Gly Asp
  1               5

<210> SEQ ID NO 12
<211> LENGTH: 9
<212> TYPE: PRT
<213> ORGANISM: Neisseria polysaccharea

<400> SEQUENCE: 12

Gly Leu Thr Tyr Leu His Leu Met Pro
  1               5

<210> SEQ ID NO 13
```

```
<211> LENGTH: 6
<212> TYPE: PRT
<213> ORGANISM: Neisseria polysaccharea

<400> SEQUENCE: 13

Asp Phe Ile Thr Asn His
 1               5

<210> SEQ ID NO 14
<211> LENGTH: 26
<212> TYPE: DNA
<213> ORGANISM: Artificial Sequence
<220> FEATURE:
<221> NAME/KEY: modified_base
<222> LOCATION: (9)
<223> OTHER INFORMATION: a, c, t, or g
<221> NAME/KEY: modified_base
<222> LOCATION: (15)
<223> OTHER INFORMATION: a, c, t, or g
<221> NAME/KEY: modified_base
<222> LOCATION: (18)
<223> OTHER INFORMATION: a, c, t, or g
<221> NAME/KEY: modified_base
<222> LOCATION: (21)
<223> OTHER INFORMATION: a, c, t, or g
<223> OTHER INFORMATION: Description of Artificial Sequence: Primer

<400> SEQUENCE: 14
gayaakwsna aksynrtngt nsargc                                         26

<210> SEQ ID NO 15
<211> LENGTH: 22
<212> TYPE: DNA
<213> ORGANISM: Artificial Sequence
<220> FEATURE:
<221> NAME/KEY: modified_base
<222> LOCATION: (2)
<223> OTHER INFORMATION: a, c, t, or g
<221> NAME/KEY: modified_base
<222> LOCATION: (5)
<223> OTHER INFORMATION: a, c, t, or g
<221> NAME/KEY: modified_base
<222> LOCATION: (8)
<223> OTHER INFORMATION: a, c, t, or g
<221> NAME/KEY: modified_base
<222> LOCATION: (17)
<223> OTHER INFORMATION: a, c, t, or g
<221> NAME/KEY: modified_base
<222> LOCATION: (21)
<223> OTHER INFORMATION: a, c, t, or g
<223> OTHER INFORMATION: Description of Artificial Sequence: Primer

<400> SEQUENCE: 15
gnkcncanat ratrccnctr na                                             22

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 16
acaaccacca tggaattagg tcgcactgat gtaac                               35

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Primer
```

```
<400> SEQUENCE: 17
gccagctgga tccgtcgact agtttatttt tgatcaagca tcttacc                47
```

We claim:

1. A glucan comprising at least 20, up to about 100,000 α-anhydroglucose units, 38–48% of which are 4-linked anhydroglucose units, 17–28% are 6-linked anhydroglucose units, and 7–20% are 4,6-linked anhydroglucose units and/or gluco-oligosaccharides containing at least two 4-linked anhydroglucose units, at least one 6-linked anhydroglucose unit and at least one 4,6-linked anhydroglucose unit.

2. A chemically modified glucan, which is obtained by 2,3-oxidation, 6-oxidation, phosphorylation, acylation, hydroxyalkylation, carboxymethylation, aminoalkylation of one or more anhydroglucose units of a glucan or gluco-oligosaccharide according to claim 2.

* * * * *